United States Patent
Suzuki et al.

(10) Patent No.: US 12,354,708 B2
(45) Date of Patent: Jul. 8, 2025

(54) ANALYSIS METHOD OF ANALYZING A NUCLEIC ACID SEQUENCE, AND A SYSTEM THAT ANALYZES A NUCLEIC ACID SEQUENCE

(71) Applicant: SYSMEX CORPORATION, Kobe (JP)

(72) Inventors: Kenichiro Suzuki, Kobe (JP); Reiko Watanabe, Kobe (JP); Mizuho Kawate, Kobe (JP); Kosuke Kai, Kobe (JP); Hiroko Onoe, Kobe (JP)

(73) Assignee: SYSMEX CORPORATION, Kobe (JP)

( * ) Notice: Subject to any disclaimer, the term of this patent is extended or adjusted under 35 U.S.C. 154(b) by 847 days.

(21) Appl. No.: 16/906,475

(22) Filed: Jun. 19, 2020

(65) Prior Publication Data

US 2020/0402612 A1    Dec. 24, 2020

(30) Foreign Application Priority Data

Jun. 19, 2019  (JP) ................. 2019-114139

(51) Int. Cl.
| | |
|---|---|
| *G16B 20/20* | (2019.01) |
| *C12Q 1/6869* | (2018.01) |
| *C12Q 1/6883* | (2018.01) |
| *C12Q 1/6886* | (2018.01) |
| *G06F 40/174* | (2020.01) |
| *G16B 30/00* | (2019.01) |
| *G16H 15/00* | (2018.01) |

(52) U.S. Cl.
CPC .......... *G16B 20/20* (2019.02); *C12Q 1/6869* (2013.01); *C12Q 1/6883* (2013.01); *C12Q 1/6886* (2013.01); *G06F 40/174* (2020.01); *G16B 30/00* (2019.02); *G16H 15/00* (2018.01); *C12Q 2600/118* (2013.01); *C12Q 2600/156* (2013.01)

(58) Field of Classification Search
CPC ........ G16B 20/20; G16B 30/00; G16B 30/10; C12Q 1/6869; C12Q 1/6883; C12Q 1/6886; C12Q 2600/118; C12Q 2600/156; G06F 40/174; G16H 15/00
See application file for complete search history.

(56) References Cited

U.S. PATENT DOCUMENTS

| | | | |
|---|---|---|---|
| 10,902,952 | B2 | 1/2021 | Lucas et al. |
| 11,527,323 | B2 | 12/2022 | Michuda et al. |
| 2003/0113756 | A1 | 6/2003 | Mertz |
| 2009/0307181 | A1 | 12/2009 | Colby et al. |
| 2019/0050530 | A1* | 2/2019 | De La Vega ........... G16B 30/00 |
| 2021/0330189 | A1 | 10/2021 | Rose et al. |

FOREIGN PATENT DOCUMENTS

| | | |
|---|---|---|
| CN | 107491666 A | 12/2017 |
| JP | 2003-067506 A | 3/2003 |
| JP | 2014-044685 A | 3/2014 |
| JP | 2015-89364 A | 5/2015 |
| JP | 2018-37093 A | 3/2018 |
| JP | 2018-38417 A | 3/2018 |
| JP | 2018-536914 A | 12/2018 |
| WO | 2018/060485 A1 | 4/2018 |
| WO | 2019/083024 A1 | 5/2019 |

OTHER PUBLICATIONS

An extended European search report (EESR) issued on Nov. 10, 2020 in a counterpart European patent application.
An Office Action issued on Dec. 28, 2022 in a related U.S. Appl. No. 16/906,269.
Scollon, Sarah et al. "Obtaining informed consent for clinical tumor and germline exome sequencing of newly diagnosed childhood cancer patients.", Genome medicine 2014, 6:69; Cited in the related USOA issued on Dec. 28, 2022.
Robert C. Green et al., "ACMG recommendations for reporting of incidental findings in clinical exome and genome sequencing", Genetics in Medicine, Jun. 20, 2013, pp. 565-574, vol. 15, No. 7, American College of Medical Genetics and Genomics; Cited in the EESR issued on Oct. 28, 2020.
Jessica N. Everett et al., "Traditional Roles in a Non-Traditional Setting: Genetic Counseling in Precision Oncology", Journal of Genetic Counseling, Mar. 1, 2014, pp. 655-660, vol. 23, No. 4, Springer, Boston, US, [retrieved on Aug. 1, 2014]; Cited in the EESR issued on Oct. 28, 2020.
Mark E. Robson et al., "American Society of Clinical Oncology Policy Statement Update: Genetic and Genomic Testing for Cancer Susceptibility", Journal of Clinical Oncology, Aug. 31, 2015, pp. 3660-3667, vol. 33, No. 31, American Society of Clinical Oncology; Cited in the EESR issued on Oct. 28, 2020.
Lacey A. Smith et al., "Reporting Incidental Findings in Clinical Whole Exome Sequencing: Incorporation of the 2013 ACMG Recommendations into Current Practices of Genetic Counseling", Journal of Genetic Counseling, Nov. 18, 2014, pp. 654-662, vol. 24, No. 4, Springer, Boston, US, [retrieved on Nov. 18, 2014]; Cited in the EESR issued on Oct. 28, 2020.
An extended European search report (EESR) issued on Oct. 28, 2020 in a counterpart European patent application.
An Office Action (JPOA) issued on Sep. 29, 2020 in a counterpart Japanese patent application.
Kristian Cibulskis et al., "Sensitive detection of somatic point mutations in impure and heterogeneous cancer samples", Nature Biotechnology, Mar. 2013, pp. 213-219, vol. 31 No. 3, Nature America, Inc.; Cited in the Specification.

(Continued)

*Primary Examiner* — G. Steven Vanni
(74) *Attorney, Agent, or Firm* — METROLEX IP LAW GROUP, PLLC; Robert L. Scott, Esq.

(57) ABSTRACT

An analysis method of analyzing a nucleic acid sequence derived from a patient sample with a computer, may include: obtaining analysis data relating to a mutation determined based on nucleic acid sequence data derived from the patient sample; and generating a first report providing information relating to the determined mutation in a first form which is different from a second form of a second report, wherein the second report provides information relating to a germline mutation among the determined mutation in the second form.

17 Claims, 37 Drawing Sheets

Specification includes a Sequence Listing.

(56) References Cited

OTHER PUBLICATIONS

An Office Action issued on Mar. 30, 2021 in a counterpart Japanese patent application.
An extended European search report (EESR) issued on Oct. 28, 2020 in a counterpart European patent application No. 20180717.9.
An Office Action (JPOA) issued on Sep. 29, 2020 in a counterpart Japanese patent application No. 2020-104354.
An extended European search report (EESR) issued on Nov. 10, 2020 in a counterpart European patent application No. 20180718.7.
An Office Action issued on Mar. 30, 2021 in a counterpart Japanese patent application No. 2020-104354.
A Chinese Office Action issued on Oct. 21, 2023 in a counterpart Chinese patent application No. 202010559682.5.
A Chinese Office Action issued on Oct. 27, 2023 in a counterpart Chinese patent application No. 202010559595.X.
An European Office Action issued on Nov. 13, 2023 in a counterpart European patent application No. 20180717.9.
An European Office Action issued on Nov. 23, 2023 in a counterpart European patent application No. 20180718.7.
A Notice of Panel Decision from Pre-Appeal Brief Review issued on Nov. 20, 2023 in a related U.S. Appl. No. 16/906,269.
An Office Action issued on Mar. 14, 2024 in a related U.S. Appl. No. 16/906,269.
A Chinese Office Action issued on Oct. 21, 2023 in a counterpart Chinese patent application.
An Office Action issued on Jul. 19, 2023 in a related U.S. Appl. No. 16/906,269.
Anonymous et al: "ACMG policy statement: updated recommendations regarding analysis and reporting of secondary findings in clinical genome-scale sequencing", Genetics in Medicine, vol. 17, No. 1, Jan. 1, 2015 (Jan. 1, 2015), pp. 68-69, XP093098294, New York ISSN: 1098-3600, DOI: 10.1038/gim.2014.151 Retrieved from the Internet: URL:https://dul.usage.elsevier.com/doi/; Cited in EPOA issued on Nov. 13, 2023 and Nov. 23, 2023 in a related European patent application.
Appelbaum Paul S. et al: "Models of Consent to Return of Incidental Findings in Genomic Research", Hastings Center Report, vol. 44, No. 4, Jun. 11, 2014 (Jun. 11, 2014), pp. 22-32, XP093098253, ISSN: 0093-0334, DOI: 10.1002/hast.328; Cited in EPOA issued on Nov. 13, 2023 and Nov. 23, 2023 in a related European patent application.
Anonymous: "National Pathology Accreditation Advisory Council Requirements For Human Medical Genome Testing Utilising Massively Parallel Sequencing Technologies", Apr. 2, 2017 (Apr. 2, 2017), XP093098244, Retrieved from the Internet: URL:https://www1.health.gov.au/internet/main/publishing.nsf/Content/FB649C2C2A42CACDCA2580A400039643/$File/Reqs%20MPS%20Technologies%202017.pdf [retrieved on Nov. 6, 2023]; Cited in EPOA issued on Nov. 13, 2023 and Nov. 23, 2023 in a related European patent.
A Chinese Office Action issued on Oct. 27, 2023 in a counterpart Chinese patent application.
An European Office Action issued on Nov. 13, 2023 in a counterpart European patent application.
An European Office Action issued on Nov. 23, 2023 in a counterpart European patent application.
The Office Action (JPOA) issued on Apr. 23, 2024 in a counterpart Japanese patent application No. 2020-120158, with English translation.
The Office Action (CNOA) issued on Sep. 30, 2024 in a counterpart Chinese patent application No. 202010559682.5.
The Office Action (CNOA) issued on Oct. 1, 2024 in a counterpart Chinese patent application No. 202010559595.X.

* cited by examiner

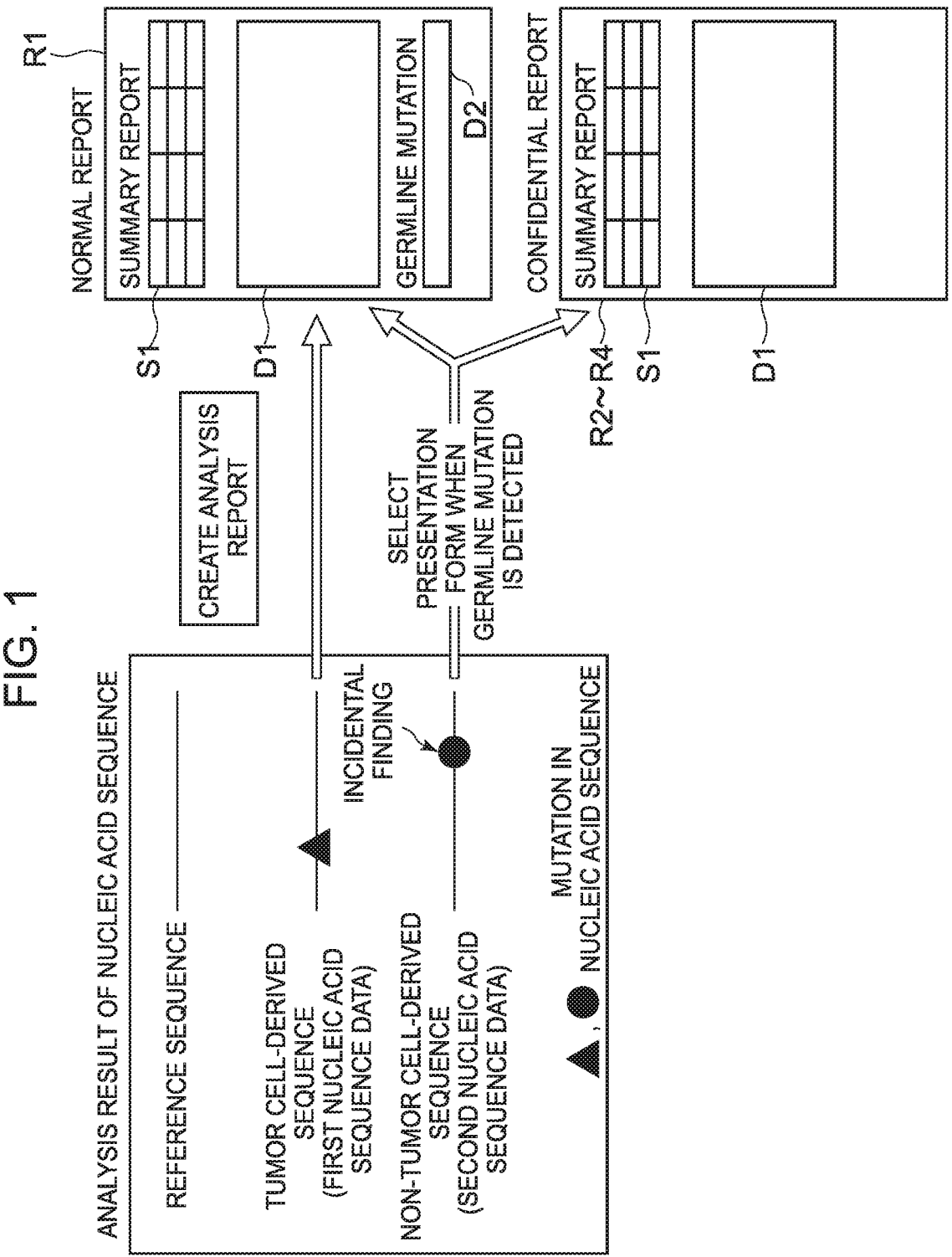

FIG. 2

SUMMARY REPORT

PATIENT ID :
ATTENDING DOCTOR NAME :
FACILITY NAME :
GENE PANEL :

DETECTED GENETIC MUTATION

| EGFR_L585R | BRAF_V600E | ………… | ………… |
|---|---|---|---|
| ………… | ………… | ………… | ………… |
| ………… | ………… | BRCA1_K1183R | ………… |

DETAILED REPORT

GENETIC MUTATION INFORMATION

| GENE NAME | MUTATION ID | CHROM | POS | REF | ALT | Annotation |
|---|---|---|---|---|---|---|
| EGFR | #1 | xx | yy | C | G | EGFRL858R |
| BRAF | #2 | aa | bb | T | A | BRAFV600E |
| ….. | … | … | … | … | … | ………… |

GERMLINE MUTATION

| GENE NAME | MUTATION ID | CHROM | POS | REF | ALT | Annotation |
|---|---|---|---|---|---|---|
| BRCA1 | #11 | … | … | … | … | BRCA1_K1183R |

FIG. 3

SUMMARY REPORT

PATIENT ID :
ATTENDING DOCTOR NAME :
FACILITY NAME :
GENE PANEL :

DETECTED GENETIC MUTATION

| EGFR_L585R | BRAF_V600E | .......... | .......... |
| .......... | .......... | .......... | .......... |
| .......... | .......... |  | .......... |

DETAILED REPORT
GENETIC MUTATION INFORMATION

| GENE NAME | MUTATION ID | CHROM | POS | REF | ALT | Annotation |
|---|---|---|---|---|---|---|
| EGFR | #1 | xx | yy | C | G | EGFRL858R |
| BRAF | #2 | aa | bb | T | A | BRAFV600E |
| ..... | ... | ... | ... | ... | ... | .......... |

FIG. 5

SUMMARY REPORT

PATIENT ID :
ATTENDING DOCTOR NAME :
FACILITY NAME :
GENE PANEL :

DETECTED GENETIC MUTATION

| EGFR_L585R | BRAF_V600E | ·········· | ·········· |
|---|---|---|---|
| ·········· | ·········· | ·········· | ·········· |
| ·········· | ·········· | BRCA1_K1183R(*) | ·········· |

DETAILED REPORT

GENETIC MUTATION INFORMATION

| GENE NAME | MUTATION ID | CHROM | POS | REF | ALT | Annotation |
|---|---|---|---|---|---|---|
| EGFR | #1 | xx | yy | C | G | EGFRL858R |
| BRAF | #2 | aa | bb | T | A | BRAFV600E |
| ····· | ··· | ··· | ··· | ··· | ··· | ·········· |

GERMLINE MUTATION (*)

| GENE NAME | MUTATION ID | CHROM | POS | REF | ALT | Annotation |
|---|---|---|---|---|---|---|
| BRCA1 | #11 | ··· | ··· | ··· | ··· | BRCA1_K1183R |

(*) PATIENT DOES NOT CONSENT TO DISCLOSE INCIDENTAL FINDING

FIG. 6

| Gene | Phenotype |
| --- | --- |
| BRCA1, BRCA2 | Hereditary Breast and Ovarian Cancer |
| TP53 | Li-Fraumeni Syndrome |
| STK11/LKB1 | Peutz-Jeghers Syndrome |
| MLH1, MSH2 | Lynch Syndrome |
| APC | Familial Adenomatous Polyposis |
| VHL | Von Hippel-Lindau Syndrome |
| RET | Multiple Endocrine Neoplasia Type 2 |
| RET | Familial Medullary Thyroid Cancer (FMTC) |
| PTEN | PTEN Hamartoma Tumor Syndrome |
| RB1 | Retinoblastoma |
| TSC1 | Tuberous Sclerosis Complex |
| SMAD4 | Juvenile Polyposis |

FIG. 10

FILE FORMAT

- SEQUENCE NAME : " Read Seq 1 "
- SEQUENCE : ...GTAAGGCAC...
- QUALITY SCORE : ...xxxxxyzxxyzzxxx...

FIG. 13A

REFERENCE SEQUENCE : • • • GCCATGGACAGAAGGCGCAGGGC (SEQ. ID. NO. 1)• • •
READ SEQUENCE 1 :      GCCATGGACAGAA    (SEQ. ID. NO.2)
READ SEQUENCE 2 :      GCCATGCACAGAA    (SEQ. ID. NO.3)

FIG. 13B

REFERENCE SEQUENCE : • • • GCCATGGA*** CAGAAGGCGCAGGGC (SEQ. ID. NO. 1) • • •
READ SEQUENCE 3 :      GCCATGGA *CAG GGCG   (SEQ. ID. NO. 4)
READ SEQUENCE 4 :      GCCATGGACGTCAGAAGGCG    (SEQ. ID. NO. 5)

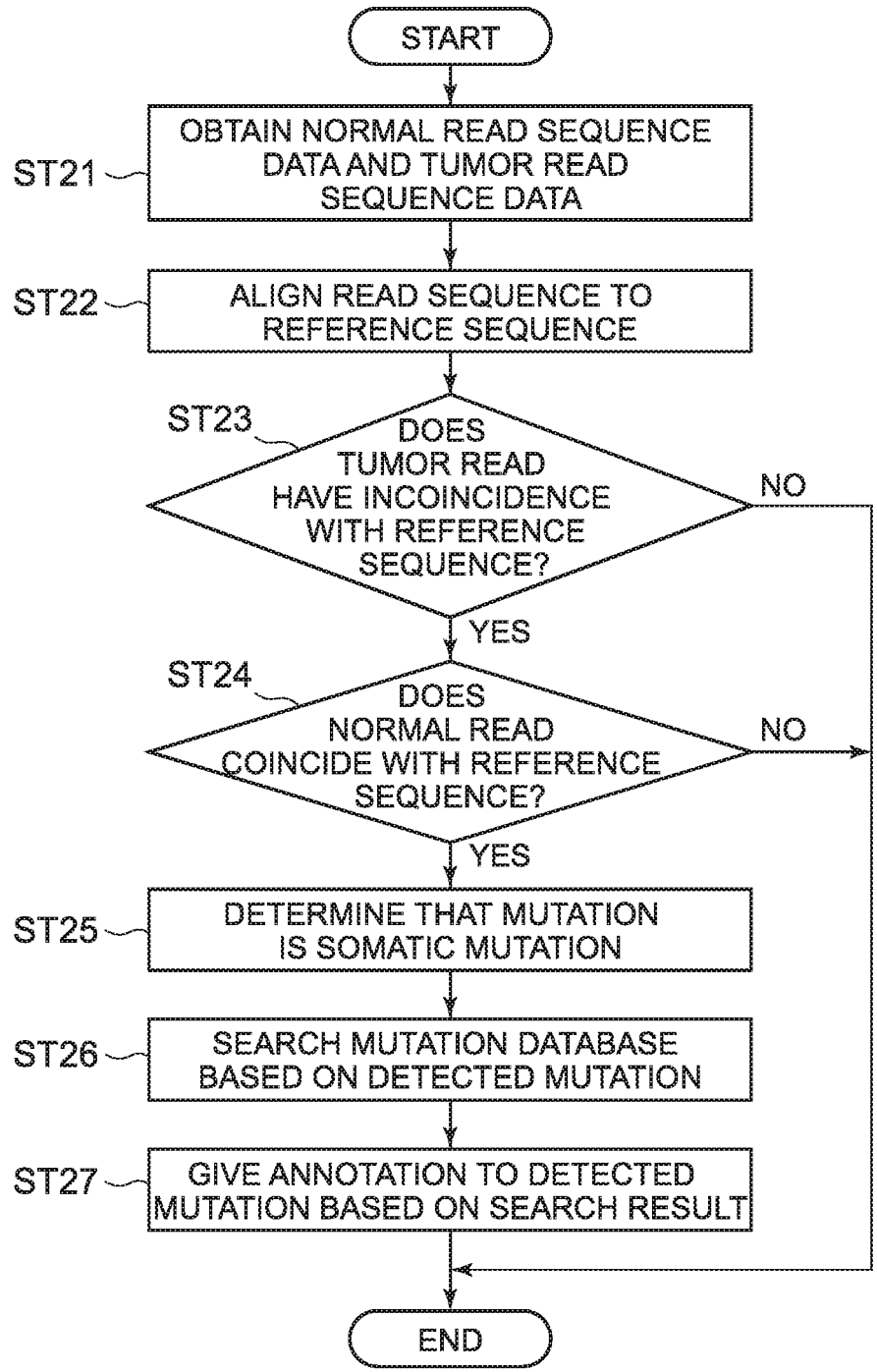

FIG. 15A

- REFERENCE SEQUENCE : ···ATGGACAGA···

- READ SEQUENCE DERIVED FROM NORMAL TISSUE : ATGGACAGA

- READ SEQUENCE DERIVED FROM TUMOR TISSUE : ATGCACAGA

FIG. 15B

- REFERENCE SEQUENCE : ···ATGGACAGA···

- READ SEQUENCE DERIVED FROM NORMAL TISSUE : ATGGACAGT

FIG. 17

```
Ex)
CHROM  POS     REF   ALT
20     3       C     G
21     4       C     CTAG
19     10      TCG   T
2      321681  G     G]17:198982]
2      321682  T     ]13:123456]T
13     123456  C     C[2:321682[
13     123457  A     [17:198983[A
```

FIG. 18

```
Ex)
MUTATION ID   CHROM   POS   REF   ALT    Annotation
#1            20      3     C     G      abc
#2            19      4     A     T      xyz
#3            xx      yy    C     G      EGFR L858R
#4            aa      bb    T     A      BRAF V600E
...
#xx           abc     ABC   G     G]p]   ALK-EML4 FUSION
#yy           xyz     XYZ   T     ]p]T   ROS1-CD74 FUSION
...
```

FIG. 28

| ID | DISCLOSURE POLICY | INFORMED CONSENT |
|---|---|---|
| AAA | DISCLOSE ALL | N/A |
| BBB | DISCLOSE ALL | CONSENT |
| CCC | CONCEAL INCIDENTAL FINDING | DISSENT |
| ... | ... | ... |

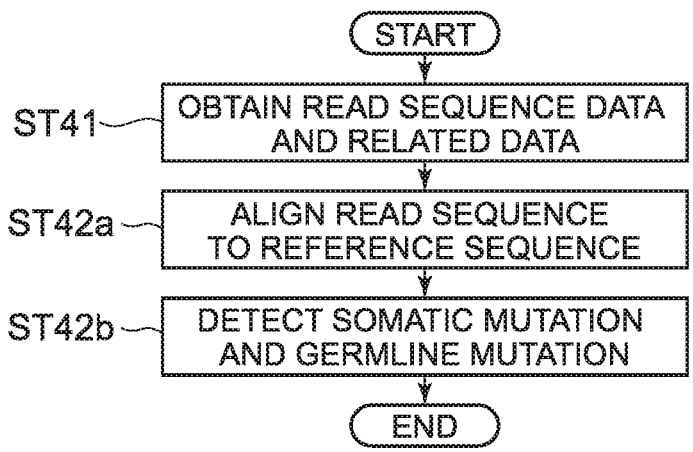
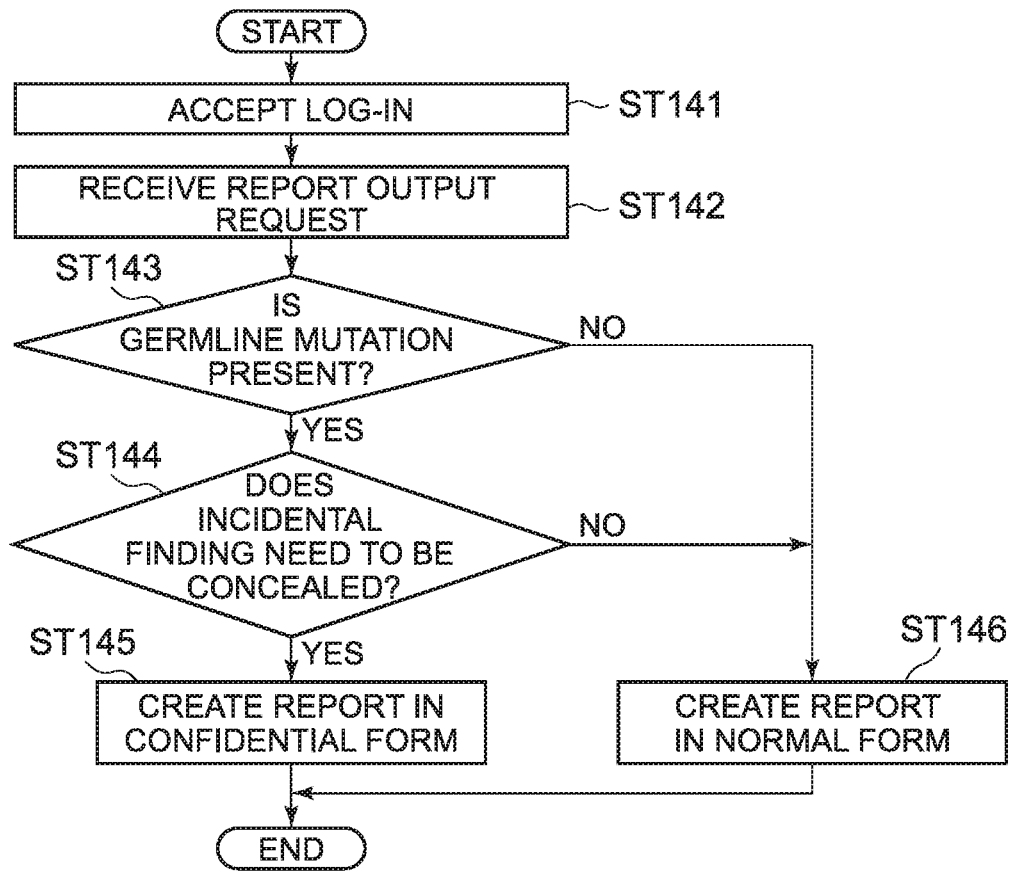

FIG. 35

| GERMLINE MUTATION | | RELATED DISEASE |
|---|---|---|
| BRCA1 | K1183R | BREAST CANCER, OVARIAN CANCER |
| ... | | ... |
| ... | | ... |
| ... | | ... |

ANALYSIS METHOD OF ANALYZING A NUCLEIC ACID SEQUENCE, AND A SYSTEM THAT ANALYZES A NUCLEIC ACID SEQUENCE

CROSS REFERENCE TO RELATED APPLICATIONS

This application claims priority from to prior Japanese Patent Application No. 2019-114139 filed with the Japan Patent Office on Jun. 19, 2019, the entire contents of which are incorporated herein by reference.

BACKGROUND

The disclosure relates to a method of analyzing a nucleic acid sequence of a patient sample, a presentation method, a presentation apparatus, and a presentation program of an analysis result of a nucleic acid sequence, and a system for analyzing a nucleic acid sequence of a patient sample.

Nature Biotechnology, 2013 March, 31(3), 213-219 describes a method of detecting a somatic mutation by comparing a read sequence derived from tumor tissues and a read sequence derived from normal tissues, the read sequences obtained by using next-generation sequencing (NGS).

A test using a read sequence derived from tumor tissues and a read sequence derived from normal tissues sometimes finds a germline mutation. A patient himself/herself may be informed of information on a germline mutation, and be treated appropriately. On the other hand, not all of patients, their relatives, attending doctors, and so on necessarily desire to know the information. From this view point, it may be required to be careful about disclosure of information on a germline mutation found in a nucleic acid test to a patient, his/her relatives, an attending doctor, and so on. One or more aspects aim to facilitate consideration about disclosure of information on a germline mutation found in a nucleic acid test to a patient, his/her relatives, an attending doctor, and so on.

SUMMARY

According to one or more aspects, an analysis method of analyzing a nucleic acid sequence derived from a patient sample with a computer, may include: obtaining analysis data relating to a mutation determined based on nucleic acid sequence data derived from the patient sample; and generating a first report providing information relating to the determined mutation in a first form which is different from a second form of a second report, wherein the second report provides information relating to a germline mutation among the determined mutation in the second form.

According to one or more aspects, a system that analyzes a nucleic acid sequence derived from a patient sample, may include: a report generate section configured to obtain analysis data relating to a mutation determined based on nucleic acid sequence data derived from the patient sample; and generate a first report providing information relating to the determined mutation in a first form which is different from a second form of a second report, wherein the second report provides information relating to a germline mutation among the determined mutation in the second form.

BRIEF DESCRIPTION OF DRAWINGS

FIG. 1 is a diagram illustrating an outline of an embodiment;

FIG. 2 is a diagram illustrating an example of a normal report form of an analysis report;

FIG. 3 is a diagram illustrating an example of a confidential report form of an analysis report;

FIG. 5 is a diagram illustrating an example of a confidential report form of an analysis report;

FIG. 6 is a diagram illustrating examples of germline mutations and diseases related to the mutations;

FIG. 10 is a diagram illustrating an example of read sequence information;

FIG. 13A is a diagram illustrating a method of calculating a rate of coincidence between a reference sequence and a read sequence;

FIG. 13B is a diagram illustrating a method of calculating a rate of coincidence between a reference sequence and a read sequence;

FIG. 14 is a flow diagram illustrating processing of detecting a somatic mutation;

FIG. 15A is a diagram illustrating an example of a nucleic acid sequence of a somatic mutation;

FIG. 15B is a diagram illustrating an example of a nucleic acid sequence of a germline mutation;

FIG. 17 is a diagram illustrating an example of a gene analysis result;

FIG. 18 is a diagram illustrating an example of output data containing an annotation;

FIG. 28 is a diagram illustrating an example of account database;

FIGS. 29A and 29B are flow diagrams illustrating processing executed by a nucleic acid sequence analysis and presentation apparatus 10C;

FIG. 35 is a diagram illustrating an example of a disease information database;

DETAILED DESCRIPTION

Figure 4:
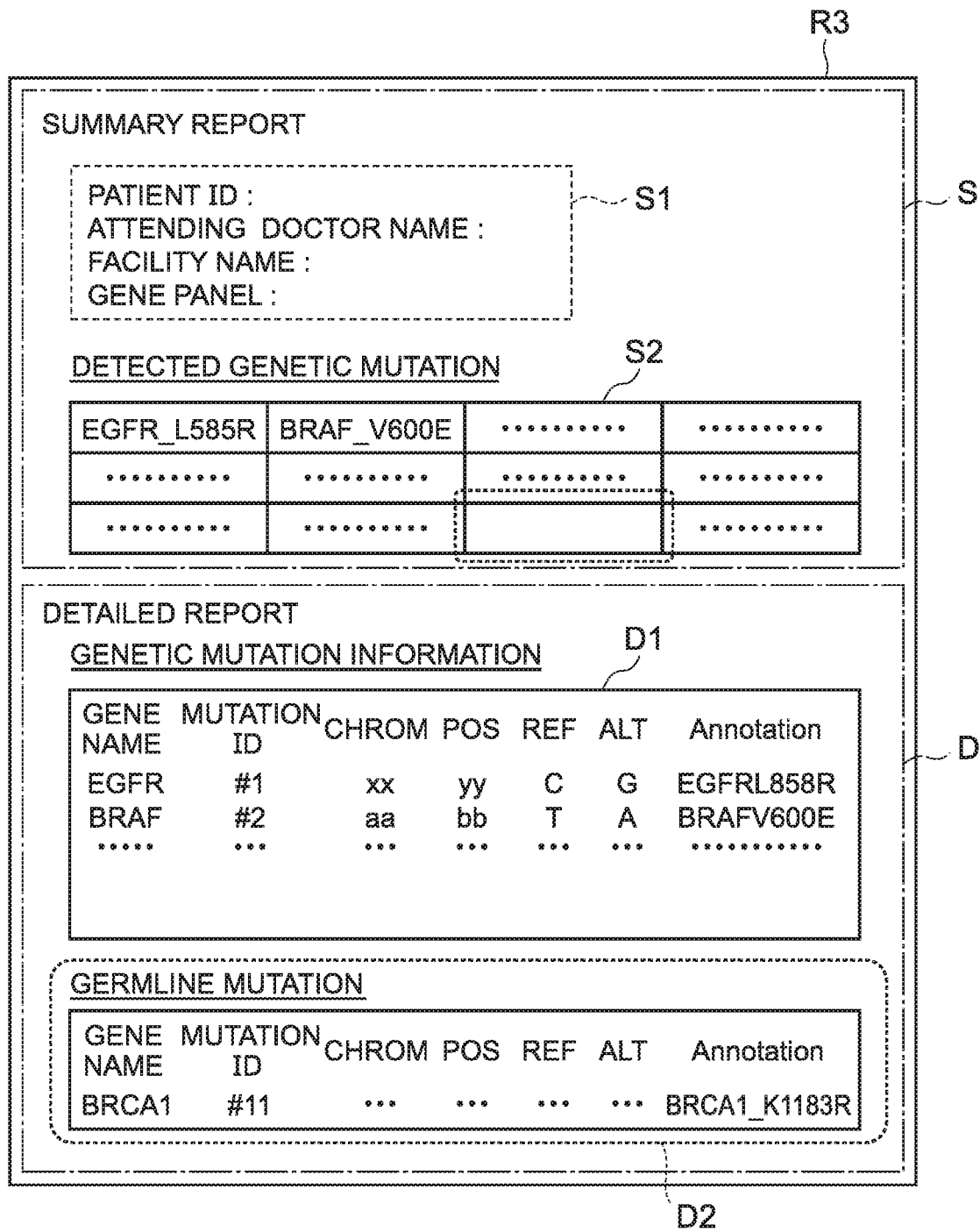
FIG. 4 is a diagram illustrating an example of a confidential report form of an analysis report.

One or more aspects relate to analysis method of analyzing a nucleic acid sequence derived from a patient sample. The analysis method include: obtaining analysis data relating to a mutation determined based on nucleic acid sequence data derived from the patient sample; and generating a first report providing information relating to the determined mutation in a first form which is different from a second form of a second report, wherein the second report provides information relating to a germline mutation among the determined mutation in the second form.

According to this configuration, when a nucleic acid sequence of a patient sample is analyzed, it is possible to select a presentation form for information on a germline mutation of a patient gene and create an analysis report in the selected form. Thus, consideration about the disclosure of information on the germline mutation can be made easily in reporting the analysis result.

One or more aspects relate to an analysis system (50) that analyzes a nucleic acid sequence of a patient sample. The analysis system includes a report generate section configured to obtain analysis data relating to a mutation determined based on nucleic acid sequence data derived from the patient sample; and generate a first report providing information relating to the determined mutation in a first form which is different from a second form of a second report, wherein the second report provides information relating to a germline mutation among the determined mutation in the second form.

According to an analysis method and an analysis system of one or more aspects, when a nucleic acid sequence of a patient sample is analyzed, it is possible to select a presentation form for information on a germline mutation and create and present an analysis report in the selected form. Thus, consideration about the disclosure of information on a germline mutation can be made easily in reporting an analysis result.

When disclosing information on a germline mutation found in a nucleic acid test to a person who has the germline mutation, consideration about the disclosure can be made easily.

Hereinafter, exemplary embodiments are described in detail with reference to the accompanying drawings. In the following description and drawings, the same reference sign denotes the same or similar constituent elements, and the explanation of the same or similar constituent elements is omitted.

Outline of Embodiment

First, with reference to FIGS. 1 to 5, an outline of an embodiment is described.

A nucleic acid sequence analysis on a patient sample is performed, for example, to detect a mutation in a nucleic acid sequence present in tumor cells in order to predict the effect of an anticancer agent on the tumor cells or predict the prognosis.

In the present description, a meaning of "a mutation in a nucleic acid sequence" contains a nucleotide replacement, insertion, and loss, a gene fusion, and so forth. Mutations to be detected are preferably nonsynonymous mutations. The nonsynonymous mutation is a mutation that causes a structural abnormality and is considered to be involved in tumorigenesis of cells.

A mutation caused in a somatic cell is called a somatic mutation and a mutation caused in a germ cell is called a germline mutation. Unlike the somatic mutation, the germline mutation may be passed on to a person in the next generation. For this reason, in the case where a patient to whom the methods of an embodiment are applied has inherited a germline mutation from the parent generation, even a sample prepared from somatic cells may contain a germline mutation.

In an example illustrated in FIG. 1, in order to detect a somatic mutation present in a tumor cell, nucleic acid sequence data derived from the tumor cell is obtained as first nucleic acid sequence data. In addition, as second nucleic acid sequence data, a nucleic acid sequence data derived from a non-tumor cell is obtained. The non-tumor cell is collected from the same patient for whom the first nucleic acid sequence data derived from the tumor cell is obtained. Next, the first nucleic acid sequence data and the second nucleic acid sequence data are compared with reference sequence data to detect whether there is a mutation in each of the nucleic acid sequences. In FIG. 1, "▲" on the tumor cell-derived sequence indicates a nucleic acid sequence mutation and can be determined as a somatic mutation because the mutation is not present in the non-tumor cell-derived sequence or the reference sequence.

On the other hand, in the case of using the second nucleic acid sequence data, a germline mutation of the patient may be detected. For example, in FIG. 1, "•" on the non-tumor cell-derived sequence indicates a nucleic acid sequence mutation and can be determined as a germline mutation because this mutation is not present in the reference sequence. Since the example illustrated in FIG. 1 is intended to detect a nucleic acid sequence mutation present in the tumor cell, the germline mutation is a mutation found incidentally or supplementarily. In the present description, a nucleic acid sequence mutation other than a mutation which presents in the tumor cell and is detected by a test may be referred to as an incidental finding. Whether or not an incidental finding and supplementary information are to be informed to a patient has to be considered carefully in the light of various things such as the type of a gene in which the mutation is detected, the type of the mutation, the severity of a disease which may be developed in association with the mutation, the prospect of treatment, and whether the patient, his/her relatives, an attending doctor, and so on desire to be informed of information on a germline mutation.

In the case where a germline mutation is detected in a nucleic acid sequence analysis of a patient sample, whether to create an analysis report in a form of a normal report R1 or to create an analysis report in any of forms exemplary illustrated as confidential reports R2, R3, and R4 is selectable in an analysis method of an embodiment.

Using FIG. 2, description is given of an example of the form of the normal report R1. The exemplary form of the normal report R1 includes an area S of a summary report as a first area (hereinafter also referred to as "summary report area S") and an area D of a detailed report as a second area (hereinafter also referred to as "detailed report area D"). The summary report area S further includes an area S1 presenting attribute information indicating information on a patient and test contents (hereinafter also referred to as "attribute information area S1") and an area S2 presenting a list of all detected genetic mutations (hereinafter also referred to as "genetic mutation list area S2"). The detailed report area D includes (i) an area D1 presenting detailed information on a mutation and a gene in which the mutation is detected in a nucleic acid sequence derived from a tumor cell (hereinafter also referred to as "genetic mutation information area D") and (ii) an area D2 presenting detailed information on a germline mutation and a gene in which the germline mutation is detected in a nucleic acid sequence derived from a non-tumor cell (hereinafter also referred to as "germline mutation information area D2").

In FIG. 2, the attribute information area S1 may present information for identifying a patient such as a patient identifier (ID), the name of the attending doctor, and the name of the medical facility, information specifying a test item such as a gene panel, and other information. The genetic mutation list area S2 may present all genetic mutations irrespective of whether each genetic mutation is a somatic mutation or a germline mutation. In the example of the genetic mutation list area S2 illustrated in FIG. 2, EGFR, BRAF, and BRCA1 indicate gene names and L585R, V600E, and K1183R indicate mutation sites. Thus, EGFR_L585R indicates that the codon at amino acid 585 of the EGFR gene is mutated from a nucleic acid sequence encoding leucine (L) to a nucleic acid sequence encoding arginine (R). The summary report area S may be presented to the patient, the attending doctor, a gene analysis expert, and so forth.

The genetic mutation information area D1 may contain information such as the name of a gene in which a mutation is detected, a mutation identifier (ID), a locus number of the gene in which the mutation is detected (containing a chromosome number CROM and a mutation position: POS), a nucleic acid sequence of a reference sequence (REF), a detected mutant sequence (ALT), and an annotation to be used for indicating the detected mutation in an analysis report.

The germline mutation information area D2 may contain information such as the name of a gene in which a mutation is detected, a mutation identifier (ID), a locus number of the gene in which the mutation is detected (containing a chromosome number CROM and a mutation position: POS), a nucleic acid sequence of a reference sequence (REF), a detected mutant sequence (ALT), and an annotation to be used for indicating the detected mutation in the analysis report. The detailed report area D may be presented to at least a gene analysis expert. The detailed report area D may not be presented to the patient and the attending doctor.

In the example in FIG. 2, the germline mutation information area D2 indicates that the BRCA1 gene has a germline mutation of "BRCA1_K1183R", and the genetic mutation list area S2 in the summary report area S also indicates "BRCA1_K1183R". In other words, in the normal report R1 exemplary illustrated in FIG. 2, "BRCA1_K1183R" which is the germline mutation indicated in the genetic mutation list area S2 is presented to the patient.

FIG. 3 illustrates an example of the form of the confidential report R2. The confidential report R2 may contain a summary report area S and a detailed report area D as in the normal report R1. The confidential report R2, however, is an example in which information on a germline mutation is not presented in either the summary report area S or the detailed report area D even if the germline mutation is detected. For example, in the form of the confidential report R2, the information on the germline mutation "BRCA1_K1183R" is not provided in the genetic mutation list area S2. In addition, detailed information on the germline mutation of "BRCA1_K1183R" is not provided in the detailed report area D, either. The confidential report R2 is the example in which the information on a germline mutation is not presented in either the summary report area S or the detailed report area D.

FIG. 4 illustrates an example of the form of the confidential report R3. The confidential report R3 may contain a summary report area S and a detailed report area D as in the normal report R1. The confidential report R3, however, is an example in which the information on the germline mutation of "BRCA1_K1183R" is not provided in the genetic mutation list area S2. On the other hand, the germline mutation information area D2 is provided in the detailed report area D. In this example, a gene analysis expert, for example, can know information on a germline mutation of a patient, but the patient himself/herself cannot know the information on the germline mutation. The confidential report R3 is the example in which information on a germline mutation is treated as confidential only in the summary report area S. Here, a reader of the detailed report area D may not be limited to the gene analysis expert, but may be any reader other than the patient such as an attending doctor and a supervisor of the attending doctor.

The above mentioned confidential reports R2 and R3 are the examples in which at least part of the information on a germline mutation held by a patient is not presented.

The following description is given of an example of presenting at least part of information on a germline mutation held by a patient, and attaching a label to draw attention to the presentation of the analysis result to the patient.

FIG. 5 illustrates an example of the form of the confidential report R4. The confidential report R4 may contain a summary report area S and a detailed report area D as in the normal report R1. In the summary report area S, the information on the germline mutation of "BRCA1_K1183R" is provided and "(*)" is attached to BRCA1_K1183R. In addition, in the detailed report area D, the information on the germline mutation is provided and "(*)" is attached to the title of "GERMLINE MUTATION". In this example, the mark "(*)" indicates that, if a germline mutation is detected, a patient corresponding to the report does not consent to know such incidental finding. Here, the mark "(*)" is an example of a label to alert the gene analysis expert, the attending doctor, or the like to the necessity to be careful about the presentation of the analysis result to the patient.

The label may be a symbol such as "*" or "!". The label may be displayed by color or be a term, a phrase, or the like such as "caution for disclosure".

In an embodiment, in the case where a germline mutation is detected in a nucleic acid sequence analysis using a patient sample, it is possible to select which form to use to create an analysis report among the multiple analysis report forms exemplary illustrated as the normal report R1 and the confidential reports R2, R3, and R4. Thus, according to an embodiment, an analysis report can be created according to a consent of patient or others, and consideration can be made easily regarding whether or not information on a germline mutation is disclosed to a patient.

[Nucleic Acid Sequence Analysis Method]

Brief Description of Analysis Method and Explanation of Terms

An embodiment relates to a method of analyzing a nucleic acid sequence of a patient sample. The analysis method may include: (process 1) obtaining first nucleic acid sequence data derived from a tumor cell collected from a patient and a second nucleic acid sequence data derived from a non-tumor cell collected from the same patient; (process 2) detecting a germline mutation based on the second nucleic acid sequence data; and (process 3) selecting a presentation form for information on the germline mutation from candidate forms and creating an analysis report in the selected form.

The tumor may include benign epithelial tumor, benign non-epithelial tumor, malignant epithelial tumor, and malignant non-epithelial tumor. The origin of a tumor is not limited. Examples of the origin of a tumor may include: respiratory tissues such as trachea, bronchi, or lungs; digestive tract tissues such as nasopharynx, esophagus, stomach, duodenum, jejunum, ileum, cecum, appendix, ascending colon, transverse colon, sigmoid colon, rectum, or anus; liver; pancreas; urinary tissues such as urinary bladder, ureter, or kidney; female reproductive system tissues such as ovaries, fallopian tubes, and uterus; mammary gland; male reproductive system tissues such as prostate; skin; endocrine tissues such as hypothalamus, pituitary gland, thyroid gland, parathyroid gland, adrenal gland; central nervous system tissues; bone and soft tissues; hematopoietic tissues such as bone marrow or lymph nodes; blood vessels; and so on.

The sample is a specimen containing nucleic acids derived from tumor cells, such as tissue, a body fluid, or excreta collected from a patient or a specimen prepared from any of them. The body fluid may be, for example, blood, bone marrow aspirate, ascitic fluid, pleural effusion, cerebrospinal fluid, or the like. The excreta may be, for example, stool or urine. It is possible to use a liquid obtained after washing part of the body of a patient, such as an intraperitoneal irrigation fluid or a colonic irrigation fluid.

An amount of nucleic acids contained in the sample is not limited, as long as the amount enables detection of a nucleic acid sequence. Meanwhile, for obtaining nucleic acid sequence data derived from non-tumor cells, a sample containing nucleic acids derived from the non-tumor cells is used. The concentration of non-tumor cells contained in the tissue, the body fluid, or the like is not limited, as long as the concentration enables detection of a nucleic acid sequence present in the non-tumor cells. In the case of tumor cells derived from a solid tumor, for example, peripheral blood, oral mucosal tissue, skin tissue, or the like may be used as a sample containing non-tumor cells. In the case of tumor cells derived from hematopoietic tissue, for example, oral mucosal tissue, skin tissue, or the like may be used as a sample containing non-tumor cells.

The sample may be collected from fresh tissue, fresh frozen tissue, paraffin-embedded tissue, and so on. The sample may be collected according to any publicly known method.

The sample containing nucleic acids derived from tumor cells and the sample containing nucleic acids derived from non-tumor cells are collected from the same patient. The sample containing nucleic acids derived from non-tumor cells and the sample containing nucleic acids derived from tumor cells may be collected at one time or different times.

The nucleic acids may be DNA or RNA.

A gene targeted in the nucleic acid sequence analysis is not limited, as long as the gene is present on a human genome. Preferably, the gene targeted in the nucleic acid sequence analysis is a gene related to the onset and prognoses of a tumor, and therapeutic effect on the tumor The germline mutation may be a mutation related to a disease or a gene polymorphism. The gene "polymorphisms" include a single nucleotide variant (SNV), a variable nucleotide of tandem repeat (VNTR), a short tandem repeat polymorphism (STRP), a microsatellite polymorphism, and so on. In Table of FIG. 6, the left column presents examples of genes in each of which a germline mutation may be detected.

The genes presented at the left column in Table of FIG. 6 are related to diseases presented at the right column in Table of FIG. 6.

The nucleic acid sequence data is not limited, as long as the nucleic acid sequence is reflected in the data. The nucleic acid sequence data may be exactly nucleic acid sequence information, or may be data indicating the structure of the nucleic acid sequence and the presence/absence of a mutation on the nucleic acid sequence or data indicating the structure of protein derived from the nucleic acid sequence. Preferably, the nucleic acid sequence data is nucleic acid sequence information.

The method for obtaining the nucleic acid sequence data is not limited, as long as the method can obtain mutation information. As for obtaining of the nucleic acid sequence data, the nucleic acid sequence information may be obtained by using a next generation sequencer to be described later. Instead, the data indicating the structure of the nucleic acid sequence and the presence/absence of a mutation on the nucleic acid sequence or the data indicating the structure of protein derived from the nucleic acid sequence may be obtained as the nucleic acid sequence data by using the PCR-Invader method, the PCR-RFLP method, the PCR-SSCP method, the Southern blotting method, the northern blotting method, the western blotting method, the FISH method, the microarray method, the immunostain method, or the like. These methods of obtaining the nucleic acid sequence are publicly known. It is preferable to use the same method to obtain the first nucleic acid sequence data derived from tumor cells and the second nucleic acid sequence data derived from non-tumor cells.

A somatic mutation and a germline mutation can be detected by comparing the first nucleic acid sequence data and the second nucleic acid sequence data with reference sequence data reported as a general sequence. For example, in the case of comparing the reference sequence data and the first nucleic acid sequence data, a mutation in the first nucleic acid sequence data can be detected by detecting a sequence in the first nucleic acid sequence data different from a sequence in the reference sequence data. Similarly, in the case of comparing the reference sequence data and the second nucleic acid sequence data, a mutation in the second nucleic acid sequence data can be detected by detecting a sequence in the second nucleic acid sequence data different from a sequence in the reference sequence data.

The information on a germline mutation is not limited, as long as the information is related to the germline mutation held by a patient for whom a nucleic acid sequence analysis is performed. For example, the information on the germline mutation may contain at least a label indicating the name of a gene in which the mutation is detected. Preferably, the information on the germline mutation may contain a label indicating the name of a gene in which the mutation is detected, and detected nucleic acid sequence information and/or information on an amino acid sequence arising from the mutation. In addition, the information may contain locus information of the gene in which the mutation is detected, the reference sequence information, and information on the mutant sequence held by the patient as discussed in the section "Outline of Embodiment". The information on the germline mutation is not limited to the information on detection of the presence/absence of the mutation, but may be, for example, information suggesting a possibility that the germline mutation may be present (for example, a mosaic mutation).

As discussed above in the section "Outline of Embodiment", the presentation form for the information on the germline mutation is selected from the candidate forms. Then, the analysis report is created according to the selected form. Here, the information on the germline mutation may be outputted and presented on a paper medium or may be outputted and presented on a display of a nucleic acid sequence analysis and presentation apparatus 10, 10A to 10E to be described later, for example. The presentation may be done by the attending doctor, the gene analysis expert, or the like, or may be done by the nucleic acid sequence analysis and presentation apparatus 10, 10A to 10E to be described later.

It is preferable to select the presentation form for the information on the germline mutation based on prescribed information. The selection of the form based on the prescribed information may be made by a user, or may be automatically made by a controller 100 in the nucleic acid sequence analysis and presentation apparatus 10, 10A to 10E based on the prescribed information. The selection of the presentation form may include selecting the form treating at least part of information on a germline mutation as confidential and/or presenting the information on the germline mutation.

The prescribed information may contain information relating to a selection of the presentation form, information on a patient, information on an analysis request, information on a test result of a nucleic acid sequence of the patient, analysis requester information, and so on.

The information relating to a selection of the presentation form may be information on a presentation form selected by the user.

The information on a patient may contain informed consent, age, sex, marital status, whether the patient has a descendant, disease name, and so on. For example, when the presentation form is selected based on a content of the informed consent, the form treating at least part of information on a germline mutation as confidential can be selected if the content indicates that the patient does not consent to know information on a germline mutation. On the other hand, if the content indicates that the patient consents to know information on a germline mutation, the form to present information on a germline mutation can be selected.

In another example, when the presentation form is selected based on the age, the form treating at least part of information on a germline mutation as confidential can be selected for an infant. In another example, if the patient is not married or may probably have a descendant after the test, the form treating at least part of information on a germline mutation as confidential can be selected.

The information on a reader of the analysis result may contain account information of the result reader or the like. For example, when a result reader has an account of a gene analysis expert, the form to present information on a germline mutation can be selected. On the other hand, when a result reader has an account other than the account of the gene analysis expert, the form treating at least part of information on a germline mutation as confidential can be selected.

The analysis requester information may contain the name of the attending doctor, the name of the gene analysis expert, the name of the medical facility, and the like. The gene analysis experts may include a clinical geneticist, a genetic counselor, and so on. For example, in the case where the attending doctor does not consent to know information on a germline mutation of a patient, the form treating at least part of information on a germline mutation as confidential can be selected.

The information on a test result of a nucleic acid sequence of the patient may contain information on a detected germline mutation. In an example in which the presentation form is selected based on the test result, the form to present information on a germline mutation can be selected if the detected germline mutation is a germline mutation present in a predetermined gene. The germline mutation present in a predetermined gene may be a germline mutation related to a certain disease, and more specifically may include a germline mutation related to a disease for which there are a treatment method and/or a prophylaxis method, a germline mutation related to a disease which the patient is suffering or suffered in the past, and so on. For example, if there are a treatment method and/or a prophylaxis method for the disease related to the detected germline mutation, the form to present information on a germline mutation can be selected. Thus, the information on the germline mutation can be used for the treatment and health management of the patient and his/her relatives. On the other hand, if there are not a treatment method and/or a prophylaxis method for the disease related to the detected germline mutation, the form treating at least part of information on a germline mutation as confidential can be selected. Here, the case where there are a treatment method and/or a prophylaxis method may include a case where a treatment method and/or a prophylaxis method have been already proposed by publications and so on but the treatment method and/or the prophylaxis method have not been practically established yet.

The presentation form may be selected based on a combination of multiple kinds of the prescribed information. For example, consider a case where the prescribed information contains sex information as the patient information and information on a detected type of mutation as the information on a test result. For example, if a disease due to a germline mutation held by a patient tends to develop in females, the form treating at least part of information on a germline mutation as confidential can be selected for a female patient. In an example in which the presentation form is selected based on the patient information and the test result, the form to present information on a germline mutation can be selected if the detected germline mutation relates to a disease that the patient is suffering or suffered in the past and the information on the germline mutation is expected to be useful for treatment and/or prophylaxis of the patient.

<Nucleic Acid Sequence Analysis System>

Figure 7:
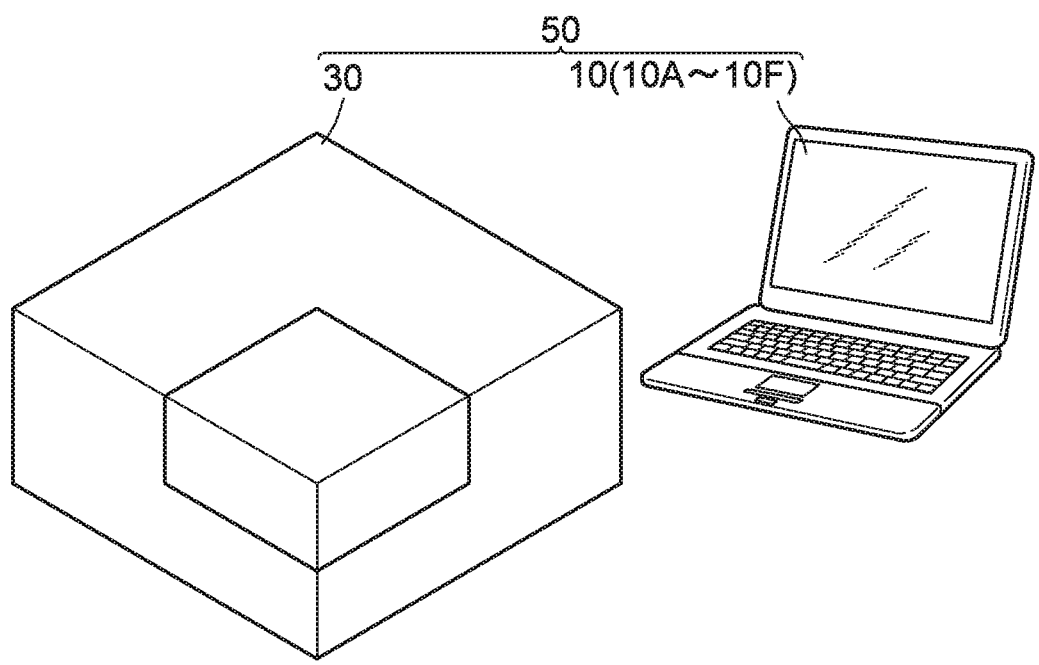
FIG. 7 is a diagram schematically illustrating a nucleic acid sequence analysis system.

FIG. 7 schematically illustrates a nucleic acid sequence analysis system 50 (hereinafter simply referred to "system 50" in some cases). The system 50 includes a nucleic acid sequence analysis and presentation apparatus 10 and a sequencer 30. The nucleic acid sequence analysis and presentation apparatus 10 and the sequencer 30 may be communicably connected to each other via a wired or wireless network.

Instead, the nucleic acid sequence analysis and presentation apparatus 10 and the sequencer 30 may be integrated into one unit. The nucleic acid sequence analysis and presentation apparatus 10 may function as a control device that controls the sequencer 30.

The sequencer 30 is a device that obtains multiple read sequences read from a nucleic acid sequence. The sequencer 30 is preferably a next generation sequencer (NGS). The next generation sequencer is publicly known.

Hereinafter, description is given of a configuration of the nucleic acid sequence analysis and presentation apparatus 10.k Hardware Configuration of Nucleic Acid Sequence Analysis and Presentation Apparatus 10

Figure 8:
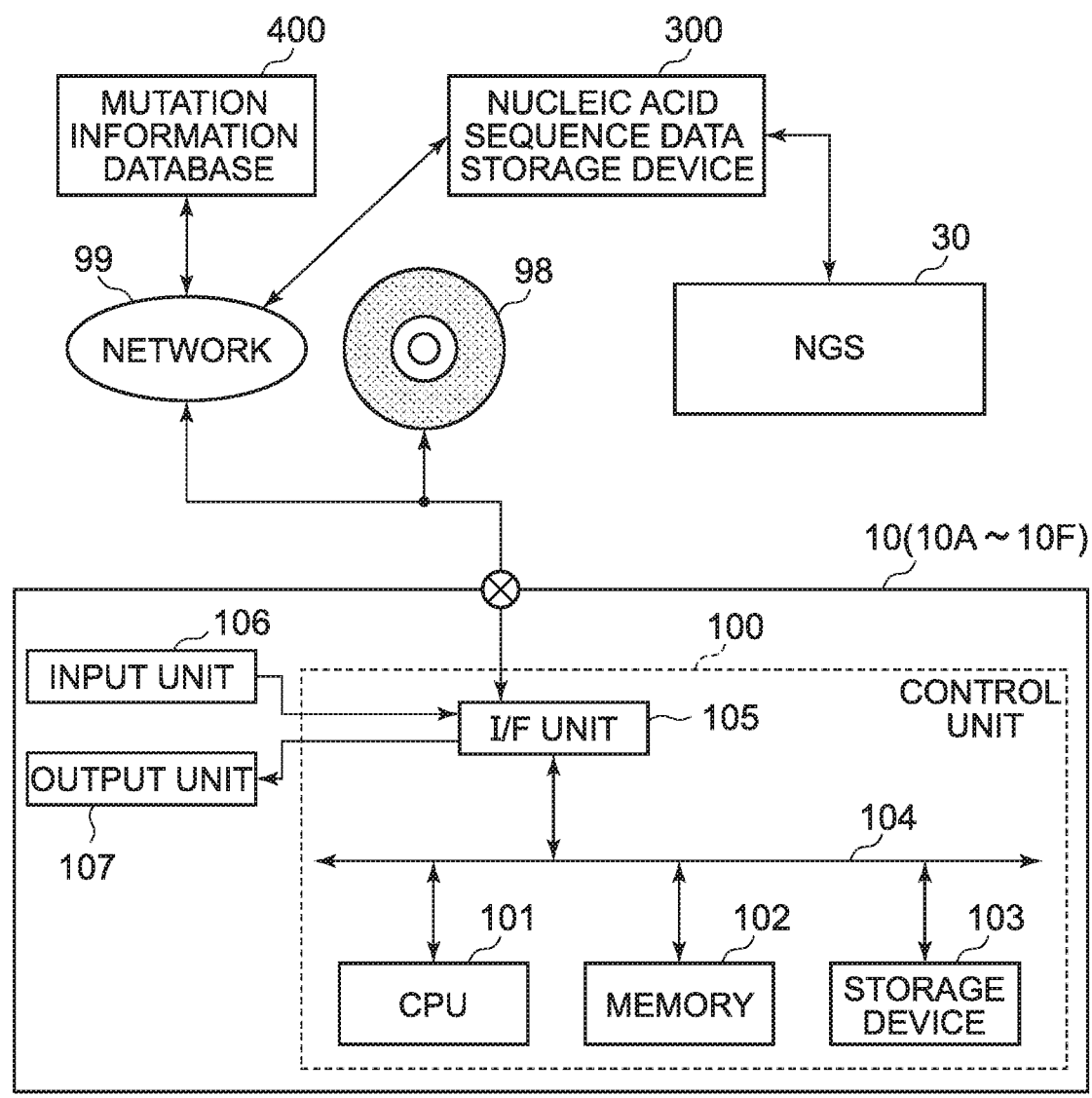
FIG. 8 is a diagram illustrating a hardware configuration example of a nucleic acid sequence analysis and presentation apparatus.

Using FIG. 8, a hardware configuration of the nucleic acid sequence analysis and presentation apparatus 10 is described. The nucleic acid sequence analysis and presentation apparatus 10 may be a general-purpose computer.

The nucleic acid sequence analysis and presentation apparatus 10 includes a control unit 100, an input unit 106, and an output unit 107.

The control unit 100 may include a central processing unit (CPU) 101 that performs data processing to be described later, a memory 102 to be used as a temporary memory area for execution of the data processing, a storage device 103 that stores a program and processed data to be described later, a bus 104 through which the foregoing components transmit data between them, and an interface (I/F) unit 105 that inputs and outputs data from and to an external apparatus. The input unit 106 and the output unit 107 are connected to the control unit 100. In an example, the input unit 106 includes a keyboard, a mouse, a touch sensor, and so on. The output unit 107 includes a display, a printer, a speaker, and so on. It is possible to use a device having the functions of the input unit and the output unit such as a touch panel in which a touch sensor and a display are integrated. The I/F unit 105 is an interface through which the control unit 100 communicates with the external apparatus.

In order to execute processes at steps to be described below with reference to FIGS. 16, 20, 23, 26, 29, 30, 32, and 35, the storage device 103 of the control unit 100 stores an application program according to an embodiment, for example, in an executable format in advance. The executable format is, for example, a format that a compiler generates from a programming language through conversion. The control unit 100 executes nucleic acid sequence analysis and presentation processing by using the program stored in the storage device 103.

In the following description, the processing executed by the control unit 100 means processing executed by the CPU 101 based on the application program stored in the storage device 103 or the memory 102 unless otherwise specified. The CPU 101 temporarily stores necessary data (such as intermediate data under processing) by using the memory 102 as a work area in a volatile manner, and stores, when necessary, data to be stored for a long time, such as analysis results, in the storage device 103 in a nonvolatile manner. The application program may be installed into the storage device 103 of the control unit 100 by being downloaded from an external storage medium 98 such as a DVD or a USB memory. The nucleic acid sequence analysis and presentation apparatus 10 is capable of connecting to and accessing a mutation information database 400 and a nucleic acid sequence data storage device 300 through a network 99.

The mutation information database 400 is an external public sequence information database, a public known-mutation information database or databases, and so on. As the public sequence information databases, information may be available on the National Center for Biotechnology Information ("NCBI") website, there are NCBI RefSeq, and NCBI GenBank, and the UCSC website Genome Browser, and so on. As the public known-mutation information databases, there are a COSMIC database available on the Sanger Institute website, NCBI databases ClinVar database, dbSNP database, and so on. The mutation information database 400 may also be a public known-mutation information database containing frequency information of each publicly known mutation for each human race or animal species. As the public known-mutation information database containing such information, there are the UCSC website HapMap Genome Browser release #28, the Center for Genomic Medicine, Kyoto University website Human Genetic Variation Browser, and The International Genome Sample Resource website 1000 Genomes database. From these databases, for example, mutation frequency information for Japanese and the like can be obtained.

Examples of a sequencing technique applicable to the sequencer 30 include sequencing techniques capable of obtaining a large number of read sequences per run, such as ion semiconductor sequencing, pyrosequencing, sequencing-by-synthesis using a reversible dye terminator, sequencing-by-ligation, and sequencing by oligonucleotide probe ligation. The sequencer 30 sequences a nucleic acid sequence to obtain read sequence information as nucleic acid sequence information. The read sequence is a nucleic acid sequence obtained by sequencing. The sequencer 30 outputs a file in a format illustrated in FIG. 10 as the read sequence information. The read sequence information may contain a sequence name, a nucleic acid sequence, a quality score of sequencing, and so on. The read sequence information obtained from nucleic acids derived from tumor cells is the first nucleic acid sequence data and the read sequence information obtained from nucleic acids derived from non-tumor cells is the second nucleic acid sequence data.

The nucleic acid sequence data storage device 300 is a computer that stores the nucleic acid sequence data obtained by the sequencer 30.

Figure 9:
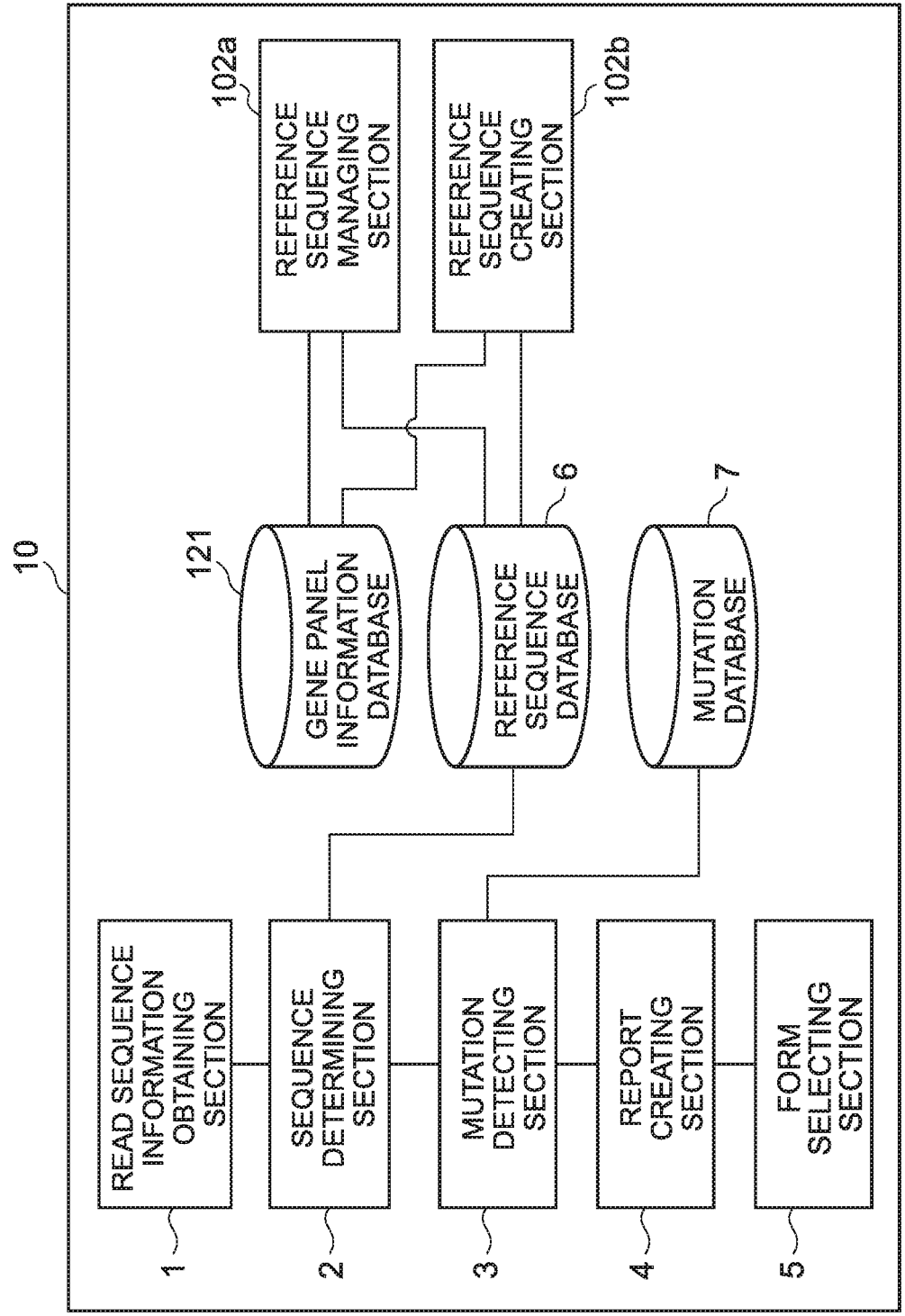
FIG. 9 is a functional block diagram illustrating a nucleic acid sequence analysis and presentation apparatus.

FIG. 9 illustrates a functional block diagram of the nucleic acid sequence analysis and presentation apparatus 10. The nucleic acid sequence analysis and presentation apparatus 10 includes a read sequence information obtaining section 1, a sequence determining section 2, a mutation detecting section 3, a report creating section 4, a form selecting section 5, a reference sequence managing section 120a, a reference sequence creating section 120b, a gene panel information database 121, a reference sequence database 6, and a mutation database 7.

Operation of Nucleic Acid Sequence Analysis and Presentation Apparatus 10

Sequence Determination

Figure 11:
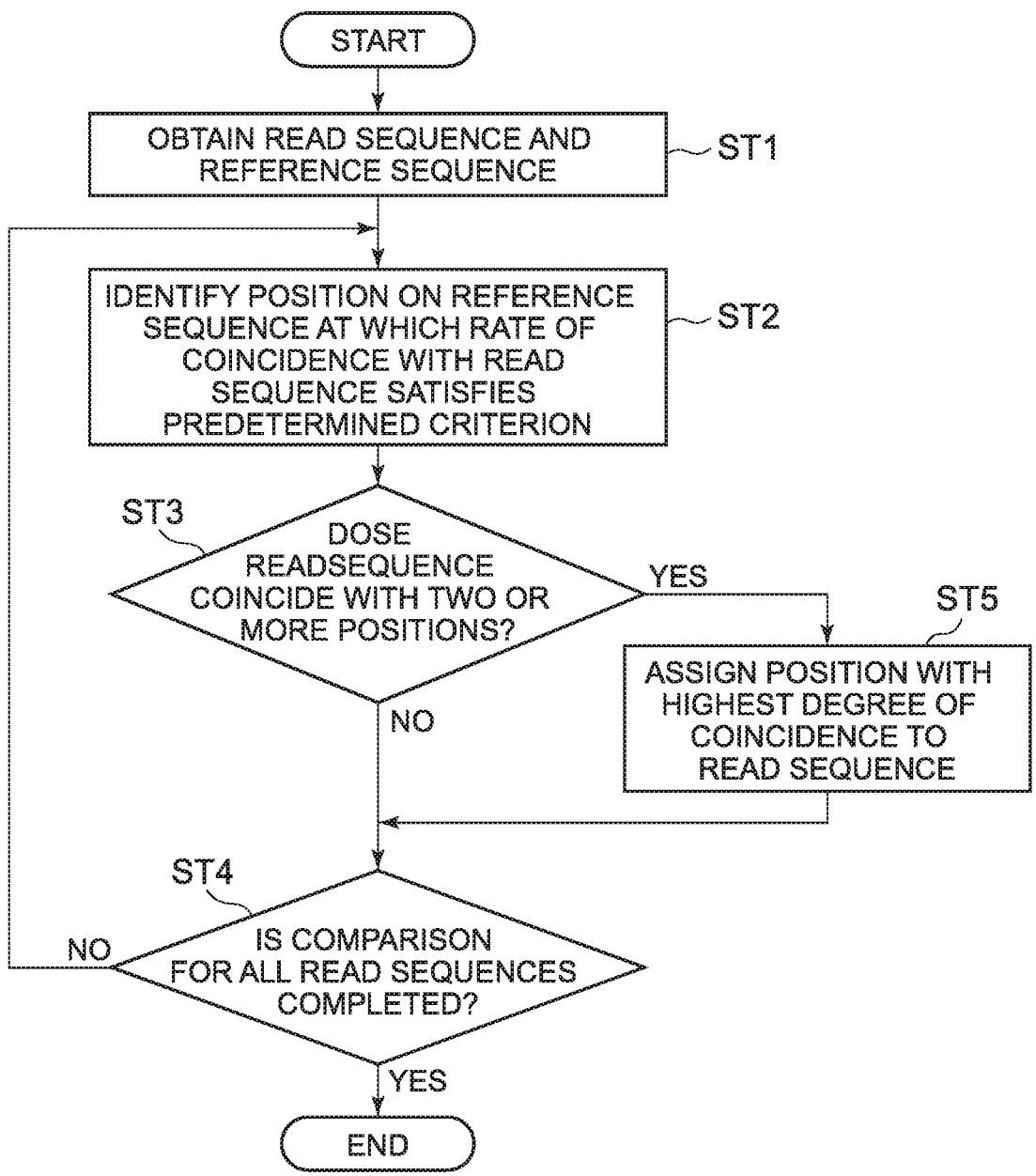
FIG. 11 is a flow diagram illustrating processing of determining a read sequence.

Using FIGS. 8, 9, and 11, description is given of an operation of the nucleic acid sequence analysis and presentation apparatus 10 for sequence determination of a read sequence. At step ST1 in FIG. 11, the read sequence information obtaining section 1 illustrated in FIG. 9 obtains read sequences from the nucleic acid sequence data storage device 300 illustrated in FIG. 8. The read sequence information obtaining section 1 may obtain the read sequences directly from the sequencer 30 illustrated in FIG. 8.

The sequence determining section 2 aligns each obtained read sequence with the reference sequence by executing steps ST2 to ST5 described below. At step ST2, the sequence determining section 2 compares the read sequence and the reference sequence to identify a position on the reference sequence at which a rate of coincidence with the read sequence satisfies a predetermined criterion. The comparing is done by mapping the read sequence to the reference sequence. The mapping means processing of aligning each read sequence with a region of the reference sequence at which the read sequence has a high degree of coincidence with the nucleic acid sequence of the reference sequence used. Here, a mutant sequence may be used in place of the reference sequence.

The reference sequence is a sequence to which the read sequence is to be mapped in order to determine (i) which region the read sequence corresponds to on the gene, and (ii) which mutation the read sequence corresponds to on the gene, or the like. For each gene to be analyzed, (1) a wild type reference sequence which is a partial sequence or the entire sequence of a wild type exon may be used as the reference sequence. Then, (2) a single mutant reference sequence in which rearranged sequences of the wild type exon sequence containing known polymorphisms and mutations are linked together may be used as the mutant sequence. The single mutant reference sequence is a sequence generated, for each gene to be analyzed, by linking together two or more rearranged sequences related to the gene to be analyzed. The single mutant reference sequence is used as the mutant reference sequence containing the rearranged sequences. Instead of the single mutant reference sequence in which two or more rearranged sequences are linked together, two or more rearranged sequences not linked together may be used as mutant reference sequences.

Figure 12:
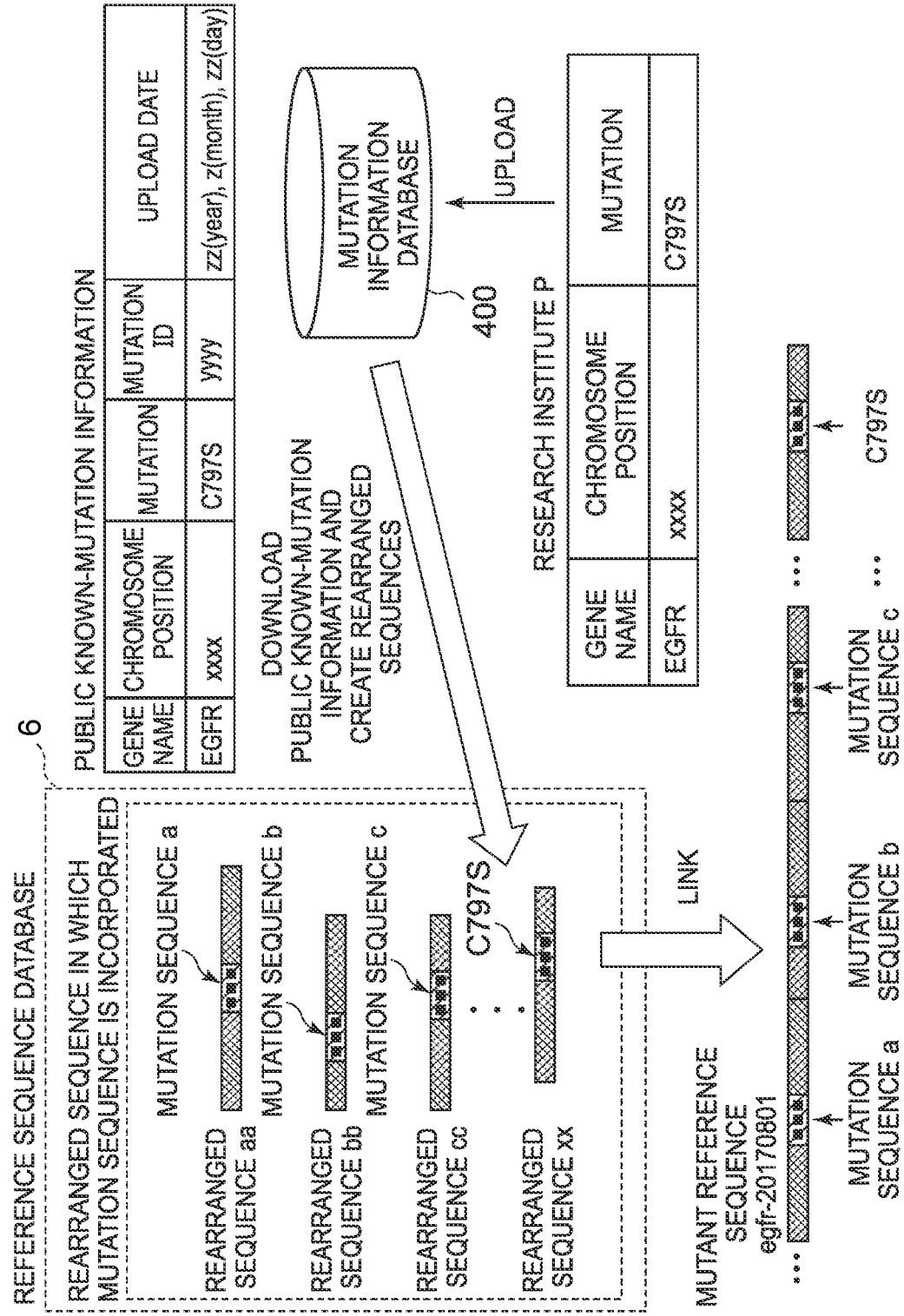
FIG. 12 is a schematic diagram illustrating a method of generating a single mutant reference sequence.

FIG. 12 illustrates an exemplary outline of a method of generating a single mutant reference sequence. FIG. 12 is a conceptual diagram for explaining the method of generating a mutant reference sequence by using public known-mutation information downloaded from the external mutation information database 400.

FIG. 12 illustrates, as an example, a case where information on a mutation "C797S" that occurred in the gene "EGFR" at chromosome position "xxxx" is newly uploaded from a research institute P to the external mutation information database 400 and is stored in the mutation information database 400. The information on the mutation "C797S" that occurred in the gene "EGFR" at chromosome position "xxxx" uploaded from the research institute P is registered as public known-mutation information in association with a mutation ID "yyyy", an upload date "zz, z, z" in a YMD format, and so on. The mutation illustrated herein as the newly uploaded information is a mutation in which cysteine at amino acid residue 797 of the protein "EGFR", which is a gene product transcribed and translated from the gene "EGFR", is replaced with serine. Note that not only the information on such a mutation but also information on polymorphisms, mutations, methylations, and the like may be collected by and stored in the external mutation information database 400.

The reference sequence managing section 120a illustrated in FIG. 9 transmits a mutation information request to the mutation information database 400 illustrated in FIG. 12 and downloads the public known-mutation information from the mutation information database 400. The reference sequence managing section 120a may be configured to download only the public known-mutation information uploaded to the mutation information database 400 after the date of the last download of the public known-mutation information. With this configuration, for example, if the reference sequence managing section 120a downloaded the public known-mutation information from the mutation information database 400 before the day "20xx/y/z", the reference sequence managing section 120a does not download the public known-mutation information which was downloaded at the previous time. In FIG. 12, if the reference sequence managing section 120a downloaded the public known-mutation information from the mutation information database 400 a day before "20xx/y/z" and transmits a mutation information request again on the day "20xx/y/z", the reference sequence managing section 120a may download only the information on the mutation "C797S" of the gene name "EGFR" which was uploaded and newly registered as the public known-mutation information on the day "20xx/y/z".

Here, the reference sequence managing section 120a may also be configured to download the public known-mutation information for all genes to be analyzed by the nucleic acid sequence analysis and presentation apparatus 10 from the mutation information database 400 on a regular basis (for example, once a month, once a week, once every two days, and so forth). Instead, the reference sequence managing section 120a may be configured to download the public known-mutation information according to an instruction from a user who uses the nucleic acid sequence analysis and presentation apparatus 10. Specifically, when the user inputs a gene panel name or a gene name or the like from the input unit 106, the reference sequence managing section 120a may download the public known-mutation information for one or more genes to be analyzed in a gene panel associated with the gene panel name or a gene associated with the gene name or the like. In this case, the reference sequence managing section 120a determines for which gene the public known-mutation information is to be downloaded in reference to the gene panel information database 121. In the case of the configuration to download the public known-mutation information according to an instruction from the user, the reference sequence managing section 120a may present the date of the last download of the public known-mutation information to the user. Thus, the user can be informed in advance whether the downloaded public known-mutation information is new and appropriate.

The reference sequence managing section 120a generates rearranged sequences based on the downloaded public known-mutation information and adds and stores the generated rearranged sequences into the reference sequence database 6. For example, the reference sequence managing section 120a uses a partial sequence or the entire sequence of a wild type and a chromosome number, a position, and a mutant sequence "a" of a mutation which are specified in the public known-mutation information to generate a rearranged sequence containing the mutant sequence "a". Thus, the rearranged sequence is a sequence in which a known polymorphism, mutation, methylation, or the like that occurred in a partial sequence or the entire sequence of a wild type exon is reproduced.

The reference sequence creating section 120b reads a rearranged sequence "aa", a rearranged sequence "bb", a rearranged sequence "cc", . . . , a rearranged sequence "xx" from the reference sequence database 6 and generates a single reference sequence by linking the rearranged sequences all together according to a predetermined linking scheme. The reference sequence database 6 also stores a wild type reference sequence in addition to the rearranged sequences in each of which a mutant sequence is incorporated and the reference sequence.

As a method of linking the rearranged sequences all together, the reference sequence creating section 120b illustrated in FIG. 9 may link the rearranged sequence "aa" (first rearranged sequence), the rearranged sequence "bb" (second rearranged sequence), the rearranged sequence "cc" (third rearranged sequence), . . . , directly to each other without inserting even one base. Instead, a spacer sequence having a predetermined length may be inserted into each of linking portions between the rearranged sequence "aa", the rearranged sequence "bb", the rearranged sequence "cc", and so on. As the spacer sequence, for example, a sequence containing 10 guanines arranged consecutively or the like may be used. Note that the spacer sequence may be formed of a string of characters other than A, T, G, and C. For example, a gene name such as "AKT1" or "EGFR", characters in the Greek alphabet such as α and β, Roman numerals such as I, VI, and IX, or a predetermined number of numerals such as "20170901" may be inserted. The insertion of the spacer sequence containing a string of characters other than A, T, G, and C as described above makes it possible to ignore the possibility of mapping a read sequence to a region over two adjacent rearranged sequences of the reference sequence, in other words, to the linking portion where the two rearranged sequences are linked to each other. Here, the character N in the English alphabet is sometimes used as a character representing a nucleotide of any of A, T, C, and G in the read sequence of the reference sequence. For this reason, it is desirable to avoid use of "N" as a spacer sequence whenever possible.

The mutant reference sequence generated by the reference sequence creating section 120b is given a reference sequence ID such for example as "egfr-20170801" and stored in the reference sequence database 6 by the reference sequence managing section 120a. In the above-described example, the reference sequence managing section 120a accesses the mutation information database 400 and downloads the information. However, an operator of the nucleic acid sequence analysis and presentation apparatus 10 may manually download the mutation information from the mutation information database 400 to the reference sequence database 6 and the mutation database 7.

Next, at step ST3 in FIG. 11, the sequence determining section 2 illustrated in FIG. 9 determines whether (i) the read sequence coincides with two or more positions on the reference sequence or the mutant reference sequence (ii) or coincides with only one position on the reference sequence or the mutant reference sequence. When the read sequence coincides with only one position on the reference sequence or the mutant reference sequence (in the case of "No"), the sequence determining section 2 proceeds to step ST4 and determines whether the comparison for all the read sequences is completed. When the comparison for all the read sequences is completed (in the case of "Yes"), it is an end of the process. When the comparison for all the read sequences is not completed (in the case of "No"), the sequence determining section 2 returns to step ST2 and continues the processing.

When the read sequence coincides with two or more positions on the reference sequence or the mutant reference sequence (in the case of "Yes") at step ST3, the sequence determining section 2 proceeds to step ST5 and assigns the position with the highest rate of coincidence (score) to the read sequence. FIG. 13A is a diagram illustrating an example of score calculation of a read sequence 1 (SEQ. ID. No. 2) and of score calculation of a read sequence 2 (SEQ. ID. No. 3) in a case in which a part of EPS8L2 gene (SEQ. ID. No. 1) is used as a reference sequence. Note that, in FIG. 13A, the 23 bases of EPS8L2 gene are only shown. As illustrated in FIG. 13A, the 23 bases include 13 bases (from 1st to 13th in SEQ. ID. No. 1) having the highest coincidence with the read sequence 1 and the read sequence 2. The score of the rate of coincidence of the read sequence 1 with the reference sequence is calculated to be 100% because all of 13 bases in the read sequence 1 coincide with the reference sequence. The score of the rate of coincidence of the read sequence 2 with the reference sequence is calculated to be 92.3% because one of the 13 bases in the read sequence 2 has a mismatch (underlined in FIG. 13A) and 12 bases out of 13 bases in the read sequence 2 coincide with the reference sequence.

In addition, the sequence determining section 2 may calculate the score indicating the rate of coincidence of the read sequence with the reference sequence such that, when the read sequence has a certain mutation (for example, InDel) as compared with the reference sequence, the score for the read sequence becomes lower than that obtained by usual calculation.

In an embodiment, the sequence determining section 2 may correct the score for a read sequence having at least one of an insertion and a deletion as compared with the reference sequence by, for example, multiplying the score obtained by the usual calculation as described above by a weight coefficient depending on the number of bases involved in InDel. The weight coefficient W may be calculated in accordance with, for example, $W=\{1-(1/100)\times(\text{the number of bases involved in InDel})\}$.

FIG. 13B is a diagram illustrating an example of score calculation of a read sequence 3 (SEQ. ID. No. 4) and of score calculation of a read sequence 4 (SEQ. ID. No. 5) in a case in which a part of EPS8L2 gene (SEQ. ID. No. 1) is used as a reference sequence. In this example, the read sequence 3 lacks the sequence "AA" as compared to the reference sequence. In the FIG. 13B, the part of the read sequence 3 corresponding to the lack is indicated by "*" representing a gap. In addition, the sequence "CGT" (underlined in FIG. 13B) is inserted into the read sequence 4 as compared with the reference sequence. In the FIG. 13B, the parts of the reference sequence and the read sequence 3 corresponding to the insertion are indicated by "" representing a gap. Because the read sequence 3 has a gap of 2 bases with respect to 17 bases that is a part of the reference sequence, the score of the rate of coincidence of the read sequence 3 with the reference sequence is calculated to be 88% in a normal calculation, and the corrected score is calculated to be 88%×0.98=86%. Furthermore, because the reference sequence has a gap of 3 bases with respect to the read sequence 4, the score of the rate of coincidence of the read sequence 4 with the reference sequence is calculated to be 85% in the normal calculation, and the corrected score is calculated to be 85%×0.96=81.6%. Note that the base length of the actual read sequence is usually 100 nt or more, but in the hypothetical cases of FIG. 13A and FIG. 13B, the read sequences 1 to 4** have short base lengths for convenience of explanation.

The sequence determining section 2 determines the position on each of the reference sequences at which the rate of coincidence with the read sequence satisfies the predetermined criterion by calculating the score of the rate of coincidence while changing the position on the reference sequence to which the read sequence is mapped. This determination may be made by using a known algorithm in this field such as dynamic programming, FASTA, or BLAST. The sequence determining section 2 proceeds to step ST4 after step ST5, and determines whether the comparison for all the read sequences is completed.

Mutation Detection

Somatic Mutation Detection

Using FIGS. 8, 9, 11, and 13 to 18 as an example, it is described an operation in which the mutation detecting section 3 detects a mutation. Using FIGS. 8, 9, 11, 13, 14, and 16, it is described an example of an operation of the mutation detecting section 3 for detecting a somatic mutation.

At step ST21 in FIG. 14, the read sequence information obtaining section 1 illustrated in FIG. 9 obtains read sequences from the nucleic acid sequence data storage device 300 illustrated in FIG. 8. The obtained read sequences include data on a read sequence derived from a non-tumor cell (normal read sequence) and a read sequence derived from a tumor cell (tumor read sequence).

At step ST22 in FIG. 14, the sequence determining section 2 aligns each of the normal read sequence and the tumor read sequence with the reference sequence. More specifically, the sequence determining section 2 executes the processes at steps ST2 to ST5 in FIG. 11.

At step ST23 in FIG. 14, the mutation detecting section 3 determines whether the tumor read has an incoincidence with the reference sequence. When the tumor read has an incoincidence with the reference sequence (in the case of "Yes"), the mutation detecting section 3 proceeds to ST24 and determines whether the normal read coincides with the reference sequence.

When the normal read coincides with the reference sequence (in the case of "Yes"), the mutation detecting section 3 proceeds to step ST25 and determines that the mutation present in the tumor read is a somatic mutation. Then, the mutation detecting section 3 identifies the gene name, the locus, and the incoincident site of the reference sequence corresponding to the read sequence having the incoincidence.

At step ST26 in FIG. 14, the mutation detecting section 3 searches the mutation database 7 based on the detected mutation. Here, the mutation database 7 may be constructed based on the external mutation information database 400 such as COSMIC or ClinVar illustrated in FIG. 8. In this example, each piece of mutation information in the database may be given meta data concerning information on a gene panel.

Each piece of the mutation information included in the mutation database 7 may contain a mutation identifier (ID), a gene name, mutation position information (for example, "CHROM" and "POS"), "REF", "ALT", and "Annotation".

The mutation ID is an identifier for identifying the mutation. In the mutation position information, "CHROM" specifies a chromosome number, and "POS" specifies a position on the chromosome number. "REF" specifies a base in a wild type and "ALT" specifies a base after the mutation. "Annotation" indicates information on the mutation. "Annotation" may be information specifying, for example, a mutation of an amino acid such as "EGFR C2573G" or "EGFR L858R". For example, "EGFR C2573G" specifies a mutation in which cysteine at residue 2573 in the protein "EGFR" is replaced with glycine.

Thus, for the mutation site detected at step ST 25 in FIG. 14, the mutation detecting section 3 can search the mutation database 7 based on the gene name having the mutation and the mutation position information.

Next, at step ST27 in FIG. 14, the mutation detecting section 3 provides an annotation to the detected mutation based on a search result at step ST26. Example of the annotation are presented in the rightmost column of a table in FIG. 18. In an embodiment, giving an annotation may be omitted. When the tumor read does not have an incoincidence ("No", at step ST23), the mutation detecting section 3 determines it is an end of this process.

After step ST27 in FIG. 14, a result with an annotation illustrated in FIG. 18 may be outputted. In addition, a gene detection result illustrated in FIG. 17 may be outputted in the genetic mutation information area D1 of any of the analysis reports R1 to R4 illustrated in FIGS. 2 to 5.

Germline Mutation Detection

Using FIGS. 8, 9, 11, 14, 16, and 18, it is described an example of an operation of the mutation detecting section 3 for detecting a germline mutation.

Figure 16:
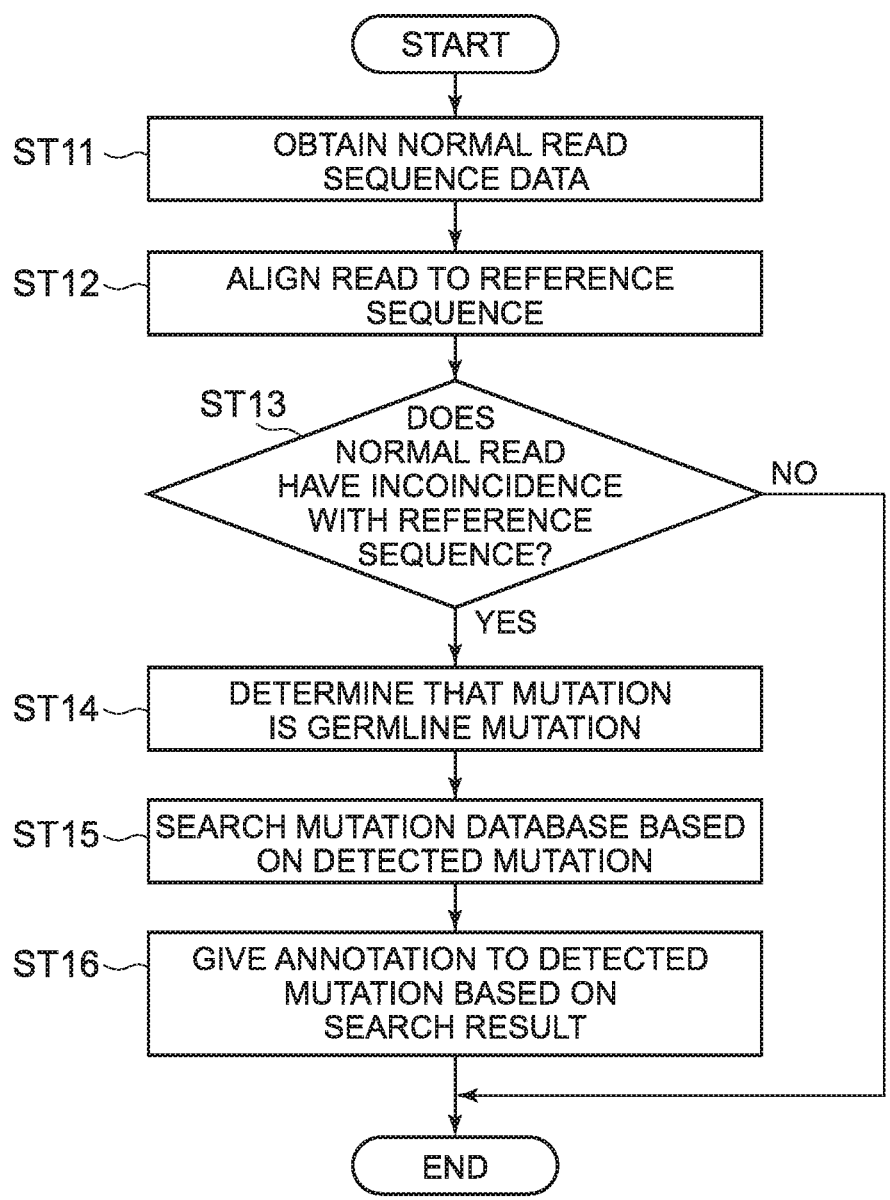
FIG. 16 is a flow diagram illustrating processing of detecting a germline mutation.

At step ST11 in FIG. 16, the read sequence information obtaining section 1 illustrated in FIG. 9 obtains a read sequence from the nucleic acid sequence data storage device 300 illustrated in FIG. 8. The obtained read sequence includes data on a read sequence derived from a non-tumor cell (normal read sequence).

At step ST12 in FIG. 16, the sequence determining section 2 aligns the normal read sequence with the reference sequence. More specifically, the sequence determining section 2 executes the processes at steps ST2 to ST5 in FIG. 11.

At step ST13 in FIG. 16, the mutation detecting section 3 determines whether the normal read has an incoincidence with the reference sequence. When the normal read has an incoincidence with the reference sequence (in the case of "Yes"), the mutation detecting section 3 proceeds to step ST14 and determines that the mutation present in the normal read is a germline mutation. Then, the mutation detecting section 3 identifies the gene name, the locus, and the incoincident site of the reference sequence corresponding to the read sequence having the incoincidence. At step ST15 in FIG. 16, the mutation detecting section 3 searches the mutation database 7 illustrated in FIG. 9 based on the detected mutation. Next, at step ST16 in FIG. 16, the mutation detecting section 3 gives an annotation to the detected mutation based on a search result at step ST15.

Steps ST14 to ST16 in FIG. 16 are the same as steps ST25 to ST27 in FIG. 14, and the above description is incorporated herein.

The mutation detecting section 3 terminates the processing when the normal read does not have an incoincidence ("No") at step ST13 in FIG. 16.

After step ST16 in FIG. 16, the result with the annotation illustrated in FIG. 18 may be outputted. The result in FIG. 18 may be outputted in the germline mutation information area D2 of any of the analysis reports R1, R3, and R4 illustrated in FIGS. 2, 4, and 5.

In the present description, to detect a mutation may mean to determine whether the read sequence has a mutation by comparing the read sequence with the reference sequence, and includes not only a case where it is determined that a somatic mutation or a germline mutation is present as a result of the comparison, but also a case where it is determined that no mutation is present as a result of the comparison.

Hereinafter, other embodiments of the nucleic acid sequence analysis and presentation apparatus 10 are described. The presentation apparatus 10 is referred to as presentation apparatuses 10A to 10E with reference numerals corresponding to respective embodiments.

(Nucleic Acid Sequence Analysis and Presentation Apparatus 10A)

Configuration of Nucleic Acid Sequence Analysis and Presentation Apparatus 10A

A hardware configuration of a nucleic acid sequence analysis and presentation apparatus 10A is the same as that of the nucleic acid sequence analysis and presentation apparatus 10 illustrated in FIG. 8. The nucleic acid sequence analysis and presentation apparatus 10A determines whether it is necessary to select the presentation form of the analysis report according to an input by the user.

Figure 19:
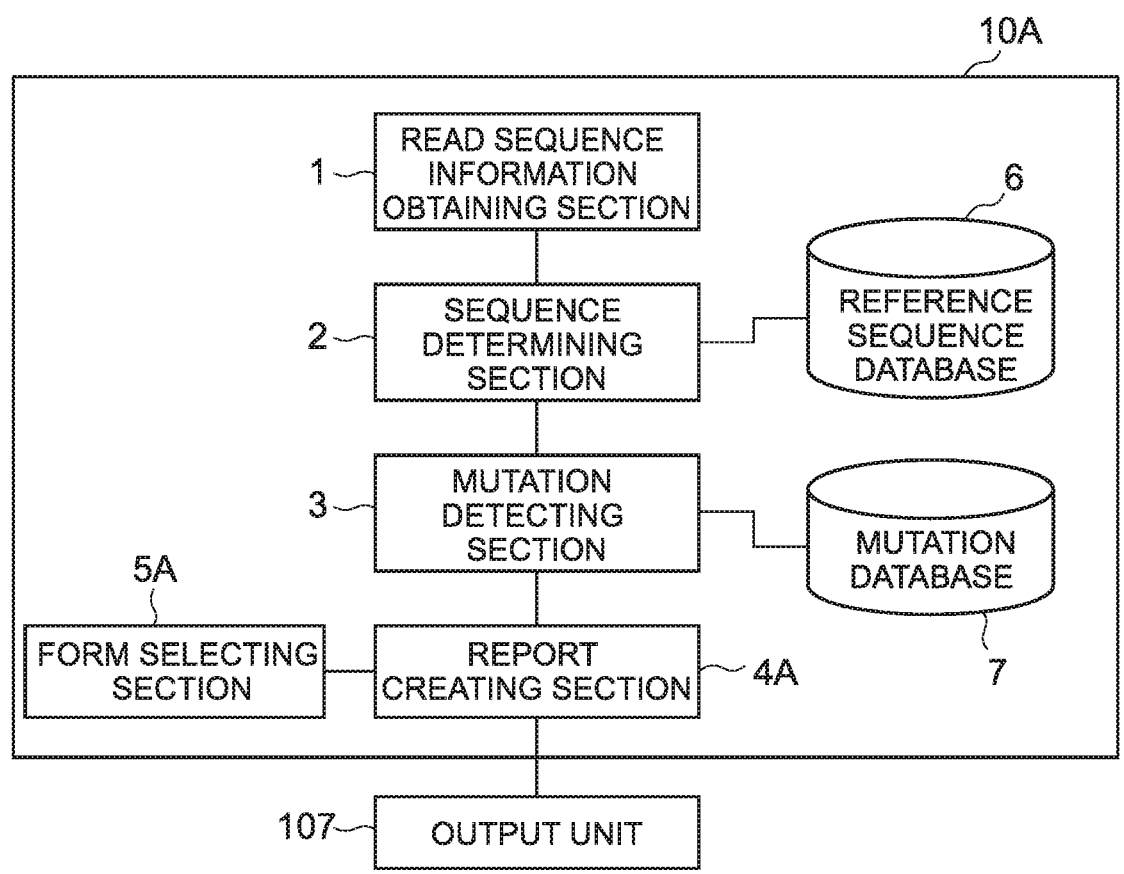
FIG. 19 is a functional block diagram illustrating a nucleic acid sequence analysis and presentation apparatus 10A.

FIG. 19 illustrates a functional block diagram for functions related to nucleic acid sequence analysis and presentation processing by the nucleic acid sequence analysis and presentation apparatus 10A. The nucleic acid sequence analysis and presentation apparatus 10A includes a read sequence information obtaining section 1, a sequence determining section 2, a mutation detecting section 3, a report creating section 4A, a form selecting section 5A, a reference sequence database 6, and a mutation database 7.

Figure 20:
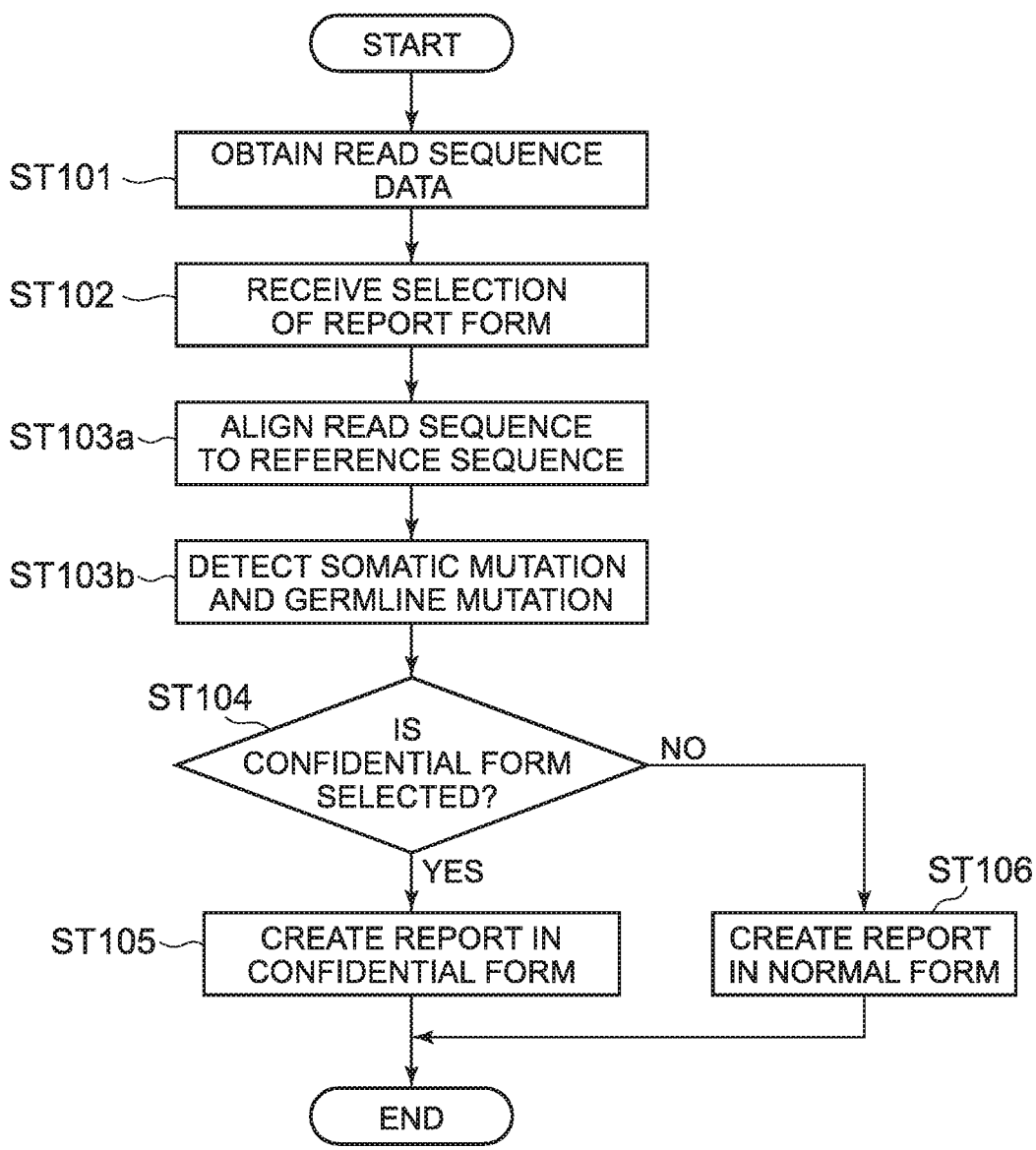
FIG. 20 is a flow diagram illustrating processing executed by a nucleic acid sequence analysis and presentation apparatus 10A.

Nucleic Acid Sequence Analysis and Presentation Processing by Nucleic Acid Sequence Analysis and Presentation Apparatus 10A FIG. 20 illustrates the nucleic acid sequence analysis and presentation processing by the presentation apparatus 10A. At step ST101, the read sequence information obtaining section 1 obtains read sequence data from the nucleic acid sequence data storage device 300 illustrated in FIG. 8. The process at step ST101 is the same as in step ST1 of FIG. 11.

Figure 21:
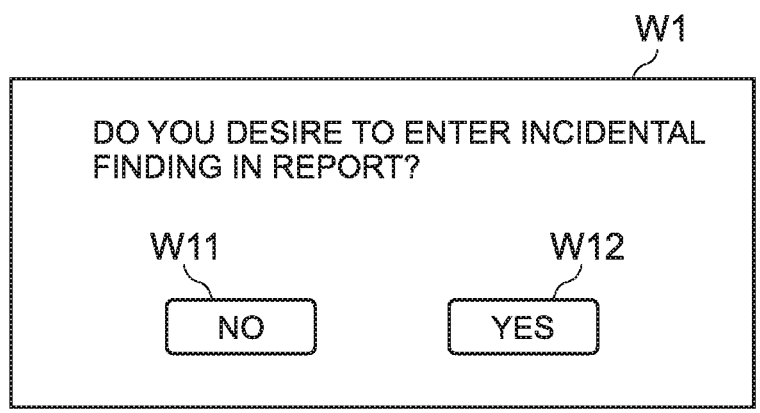
FIG. 21 is a diagram illustrating an example of a dialog for prompting a user to select whether it is necessary to report an incidental finding.

At step ST102, the form selecting section 5A receives a selection of a report form as the presentation form of the analysis report made by the user. FIG. 21 illustrates an example of a report form selection dialog W1. The form selecting section 5A causes the output unit 107 illustrated in FIG. 8 to display the selection dialog W1. In the exemplary selection dialog W1, an inquiry about whether to enter an incidental finding in a report is displayed. The phrase for the inquiry may be another phrase such as "Do you desire to enter a germline mutation in a report?" The user selects a "NO" icon W11 or a "YES" icon W12 in the selection dialog W1 by clicking it with a mouse as the input unit 106 or touching it on a touch panel as the input unit 106. The form selecting section 5A receives the selection of the icon made by the user.

At step ST 103a in FIG. 20, the sequence determining section 2 executes the processes at steps ST2 to ST5 in FIG. 11, and aligns each of the normal read sequence and the tumor read sequence with the reference sequence.

At step ST103b in FIG. 20, the mutation detecting section 3 executes the processes at steps ST23 to ST27 in FIG. 14 and steps ST13 to ST16 in FIG. 16 to detect a somatic mutation and a germline mutation and give the annotations.

When the selection of the "NO" icon W 11 is received at step ST102 in FIG. 2, the form selecting section 5A determines that the confidential form is selected (Yes) at step ST104. In this case, the processing proceeds to step ST105, and the report creating section 4A creates a report in the confidential form. Which form to use to create an analysis report among the forms of the confidential reports R2, R3, and R4 may be determined in advance by the user or a selection of the form made by the user may be received at step ST102.

When the selection of the "YES" icon W 12 is received at step ST102, the form selecting section 5A determines that the confidential form is not selected (No) at step ST104. In this case, the processing proceeds to step ST106, and the report creating section 4A creates the normal report R1 illustrated in FIG. 21 in the normal form. Here, step ST102 and step ST103 may be executed in any order.

(Nucleic Acid Sequence Analysis and Presentation Apparatus 10B)

Configuration of Nucleic Acid Sequence Analysis and Presentation Apparatus 10B

A hardware configuration of the nucleic acid sequence analysis and presentation apparatus 10B is the same as that of the nucleic acid sequence analysis and presentation apparatus 10 illustrated in FIG. 8. The nucleic acid sequence analysis and presentation apparatus 10B determines whether it is necessary to select the presentation form of the analysis report according to prescribed information obtained as related data. The prescribed information is the same as described in the above section <Brief Description of Analysis Method and Explanation of Terms>.

Figure 22:
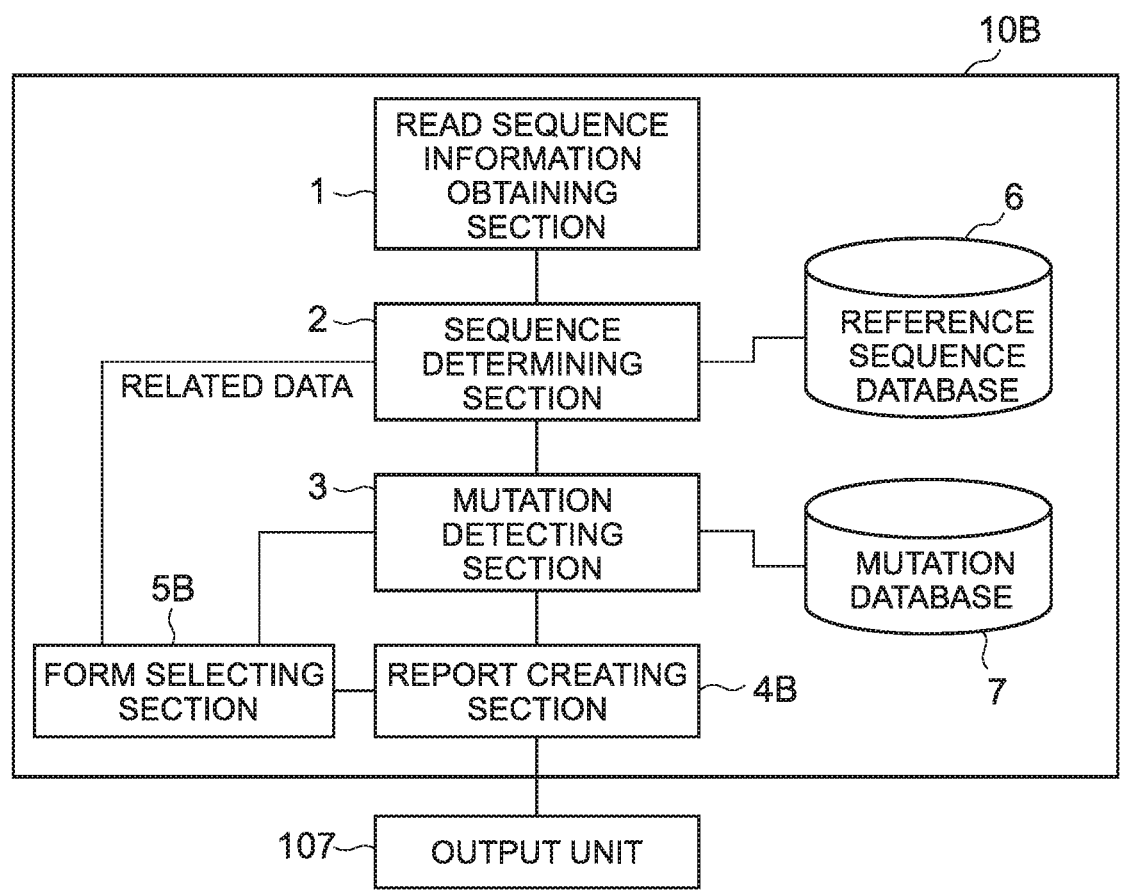
FIG. 22 is a functional block diagram illustrating a nucleic acid sequence analysis and presentation apparatus 10B.

FIG. 22 illustrates an exemplary functional block diagram for functions related to nucleic acid sequence analysis and presentation processing by the nucleic acid sequence analysis and presentation apparatus 10B. The nucleic acid sequence analysis and presentation apparatus 10B includes a read sequence information obtaining section 1, a sequence determining section 2, a mutation detecting section 3, a report creating section 4B, a form selecting section 5B, a reference sequence database 6, and a mutation database 7. The read sequence information obtaining section 1, the sequence determining section 2, the mutation detecting section 3, the report creating section 4B, the form selecting section 5B, the reference sequence database 6, and the mutation database 7 have the same functions as the blocks with the same reference numerals illustrated in FIG. 19.

Figure 23:
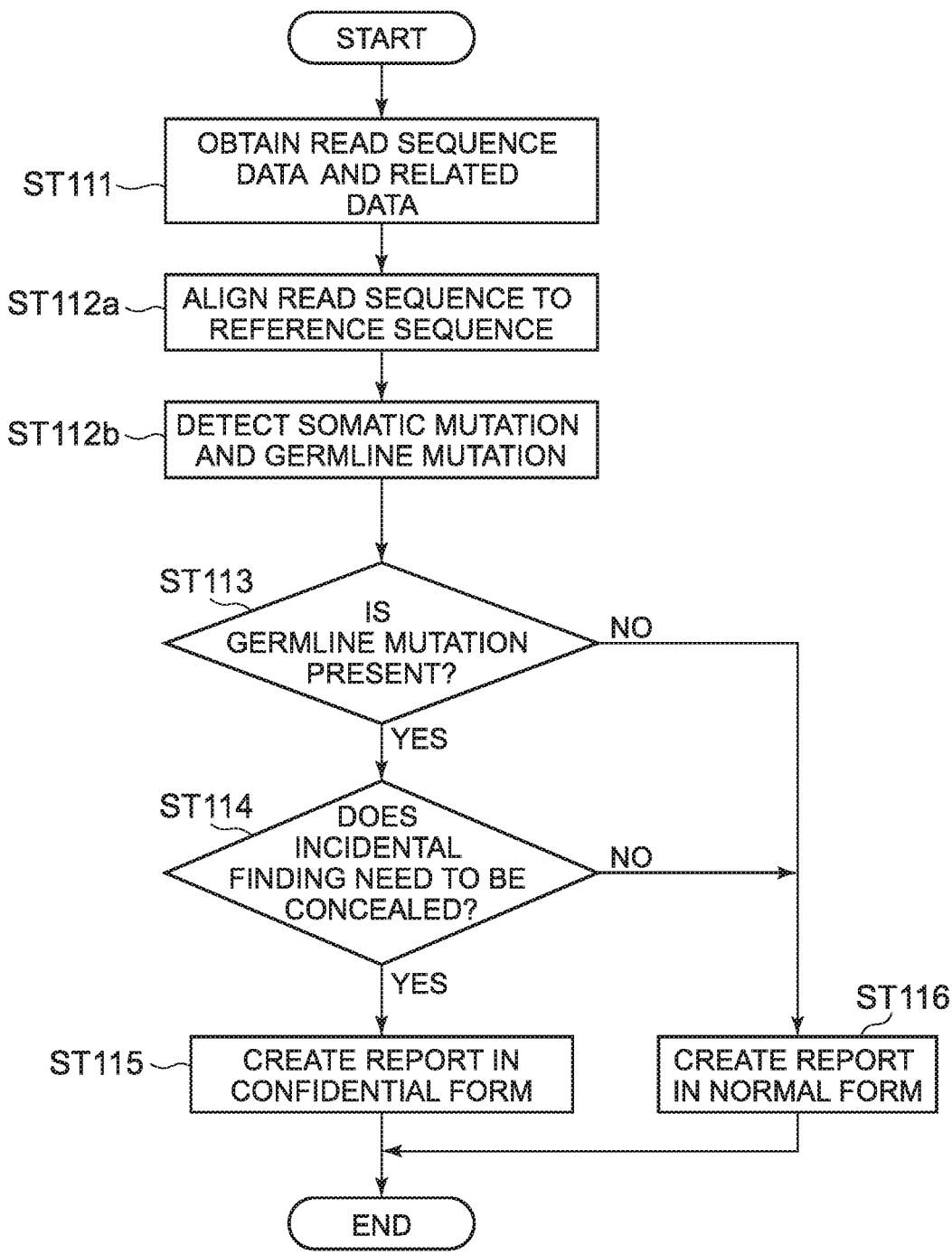
FIG. 23 is a flow diagram illustrating processing executed by a nucleic acid sequence analysis and presentation apparatus 10B.

Nucleic Acid Sequence Analysis and Presentation Processing 1 by Nucleic Acid Sequence Analysis and Presentation Apparatus 10B FIG. 23 illustrates the nucleic acid sequence analysis and presentation processing by the nucleic acid sequence analysis and presentation apparatus 10B. At step ST111, the read sequence information obtaining section 1 obtains read sequence data and related data by causing the output unit 107 to display a dialog W2 illustrated in FIG. 24 or a dialog W3 illustrated in FIG. 25, and receiving an input in the dialog by the user.

Figure 24:
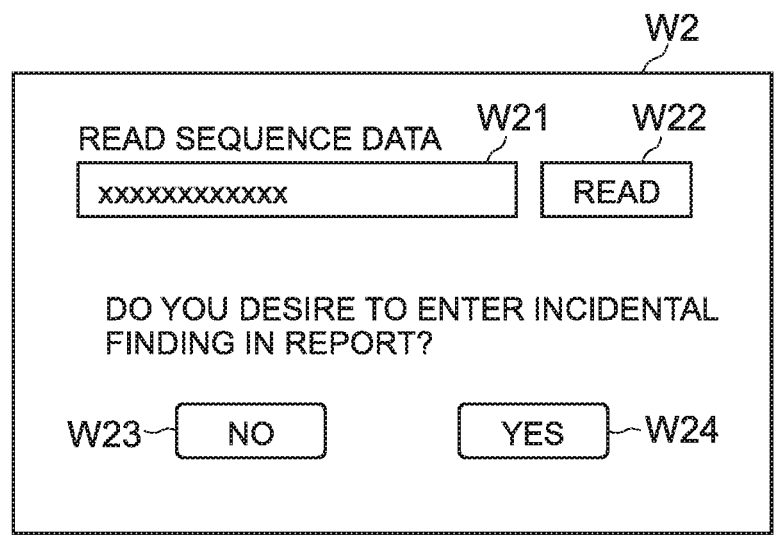
FIG. 24 is a diagram illustrating an example of a dialog for prompting a user to select whether it is necessary to report an incidental finding.

FIG. 24 illustrates an example in which the prescribed information is information concerning the presentation form selected by the user. The dialog W2 contains a read sequence name input area W21 for inputting the sequence name of read sequence data (see FIG. 10), an icon W22 for starting read sequence data reading processing, and a "NO" icon W23 and a "YES" icon W24 for prompting the user to select whether to enter an incidental finding in a report. When the user inputs the sequence name of read sequence information for which the user desires to create an analysis report to the read sequence name input area W21 and selects the icon W22 by clicking it with the mouse or the like or touching it on the touch panel, the read sequence information obtaining section 1 reads the read sequence information. In the read sequence name input area W21, pieces of read sequence information created by the sequencer 30 may be displayed in a pull-down list format. In addition, the form selecting section 5A receives a selection of whether to enter an incidental finding in a report when the user selects the "NO" icon W23 or the "YES" icon W24 by clicking it with the mouse or the like or touching it on the touch panel.

Figure 25:
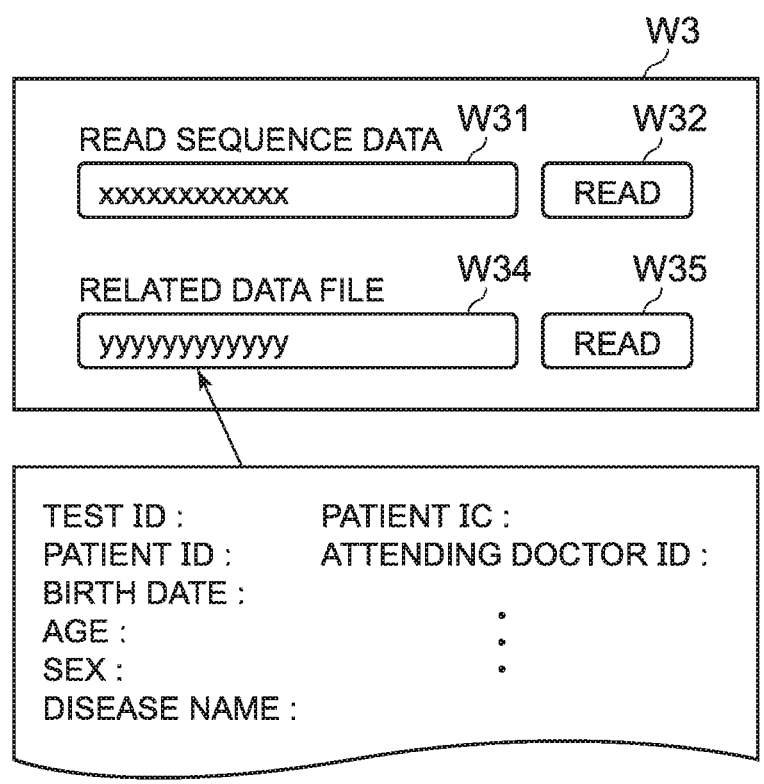
FIG. 25 is a diagram illustrating an example of a dialog for selecting whether it is necessary to report an incidental finding based on prescribed information.

FIG. 25 illustrates an example in which the prescribed information contains the information on a patient, the information on an analysis request, the analysis requester information, and so on. A dialog W3 contains a read sequence name input area W31 for inputting the sequence name of read sequence data (see FIG. 10), an icon W32 for starting read sequence data reading processing, a related data file name input area W34 to be used to input the prescribed information, and an icon W35 for starting related data file reading processing. When the user inputs the sequence name of read sequence information for which the user desires to create an analysis report to the read sequence name input area W31 and selects the icon W32 by clicking it with the mouse or the like or touching it on the touch panel, the read sequence information obtaining section 1 reads the read sequence information. In the read sequence name input area W31, pieces of read sequence information created by the sequencer 30 may be displayed in a pull-down list format. When the user inputs the name of a desired related data file to the related data file name input area W34 and selects the icon W35 by clicking it with the mouse or the like or touching it on the touch panel, the form selecting section 5A reads the related data file. Here, in the example illustrated in FIG. 25, the related data file contains a test ID for identifying a test item, a patient ID for identifying a patient, the birth date, the age, the sex, and the disease name of the patient, a content of informed consent (IC) of the patient, an attending doctor ID, and so on.

At step ST112a in FIG. 23, the sequence determining section 2 executes the processes at steps ST2 to ST5 in FIG. 11 to align each of the normal read sequence and the tumor read sequence with the reference sequence.

At step ST112b in FIG. 23, the mutation detecting section 3 executes the processes at steps ST23 to ST27 in FIG. 14 and steps ST13 to ST16 in FIG. 16 to detect a somatic mutation and a germline mutation and give the annotations.

The form selecting section 5B determines whether a germline mutation is detected at step ST113 based on the information obtained at step ST112b. When it is determined that the germline mutation is present at step ST113 (in the case of "Yes"), the processing proceeds to step ST114. The form selecting section 5B determines whether it is necessary to treat an incidental finding as confidential based on the related data inputted at step ST111. Specifically, when the "NO" icon W23 in the dialog W2 illustrated in FIG. 24 is selected at step ST111, the form selecting section 5B determines that it is necessary to treat the incidental finding as confidential ("Yes", at step ST114). Alternatively, at step ST114, the form selecting section 5B determines whether it is necessary to treat the incidental finding as confidential based on the information in the file with the name, an input of which is received through the related data file name input area W34 illustrated in FIG. 25. When the form selecting section 5B determines that it is necessary to treat the incidental finding as confidential ("Yes", at step ST114), the processing proceeds to step ST115, and the report creating section 4B creates the report in the confidential form. Which form to use to create an analysis report among the forms of the confidential reports R2, R3, and R4 may be determined in advance by the user or a selection of the form made by the user may be received at step ST111.

When the mutation detecting section 3 does not detect any germline mutation at step ST113 or when the form selecting section 5B determines that it is unnecessary to treat the incidental finding as confidential ("No", at step ST114), the processing proceeds to step ST116, and the report creating section 4B creates the normal report R1 illustrated in FIG. 1 in the normal form.

Figure 26:
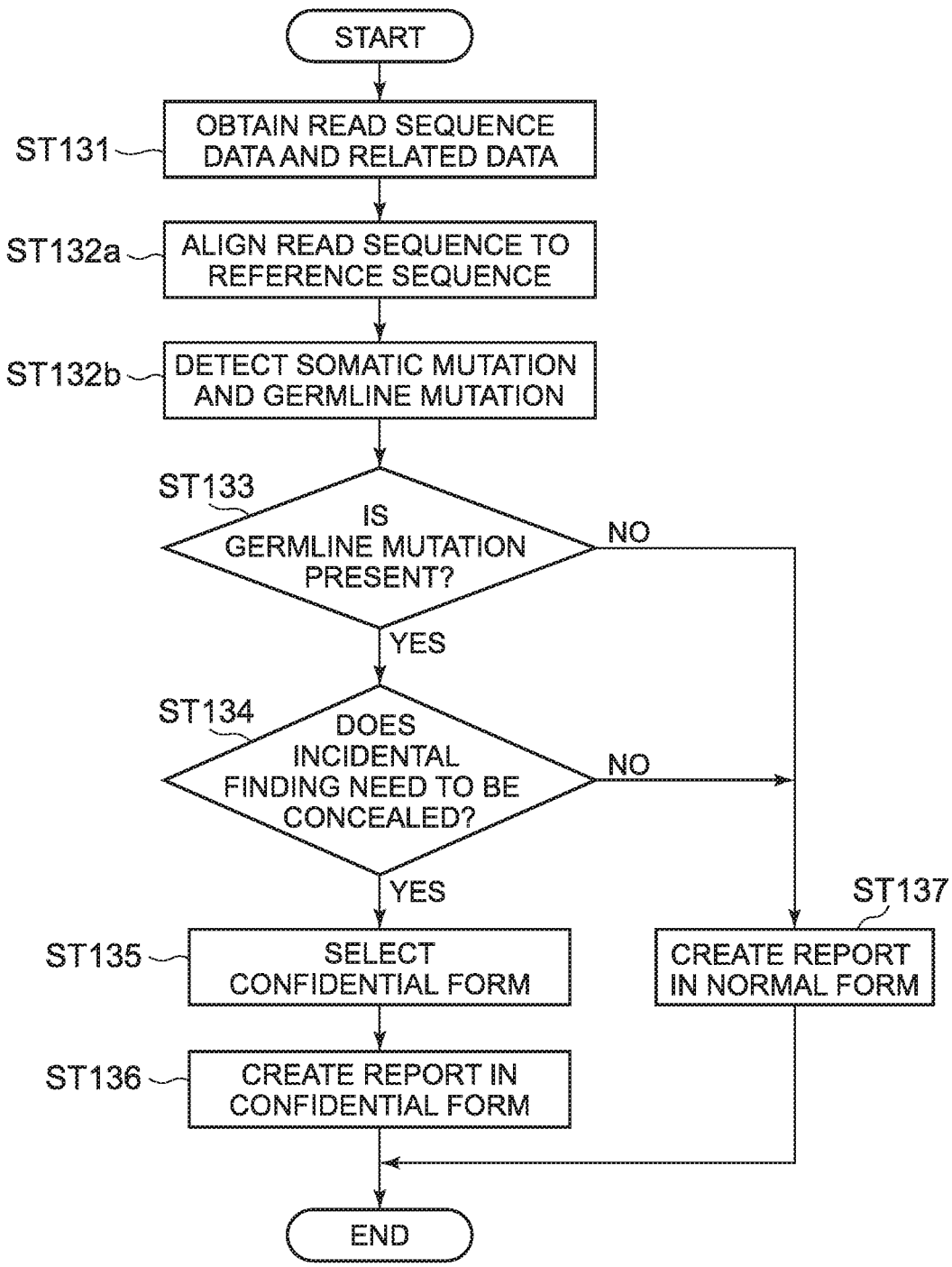
FIG. 26 is a flow diagram illustrating other processing executed by a nucleic acid sequence analysis and presentation apparatus 10B.

Nucleic Acid Sequence Analysis and Presentation Processing 2 by Nucleic Acid Sequence Analysis and Presentation Apparatus 10B FIG. 26 illustrates a modified example of the nucleic acid sequence analysis and presentation processing by the nucleic acid sequence analysis and presentation apparatus 10B. Steps ST131 to ST134 in FIG. 26 are the same as steps ST111 to ST114 in FIG. 23.

When determining that it is necessary to treat the incidental finding as confidential ("Yes" at step ST134), the form selecting section 5B illustrated in FIG. 22 proceeds to step ST135 and receives a user's selection of which form to use to create an analysis report among the forms of the confidential reports R2, R3, and R4. The report creating section 4B creates the report in the received form at step ST136.

When the mutation detecting section 3 does not detect any germline mutation at step ST133 or when the form selecting section 5B determines that it is unnecessary to treat the incidental finding as confidential ("No", at step ST134), the processing proceeds to step ST137, and the report creating section 4B creates the normal report R1 illustrated in FIG. 2 in the normal form.

(Nucleic Acid Sequence Analysis and Presentation Apparatus 10C)

Configuration of Nucleic Acid Sequence Analysis and Presentation Apparatus 10C

A hardware configuration of a nucleic acid sequence analysis and presentation apparatus 10C is the same as that of the nucleic acid sequence analysis and presentation apparatus 10 illustrated in FIG. 8. The nucleic acid sequence analysis and presentation apparatus 10C determines whether it is necessary to select the presentation form of the analysis report according to the account information of a result reader in the prescribed information obtained as the related data.

Figure 27:
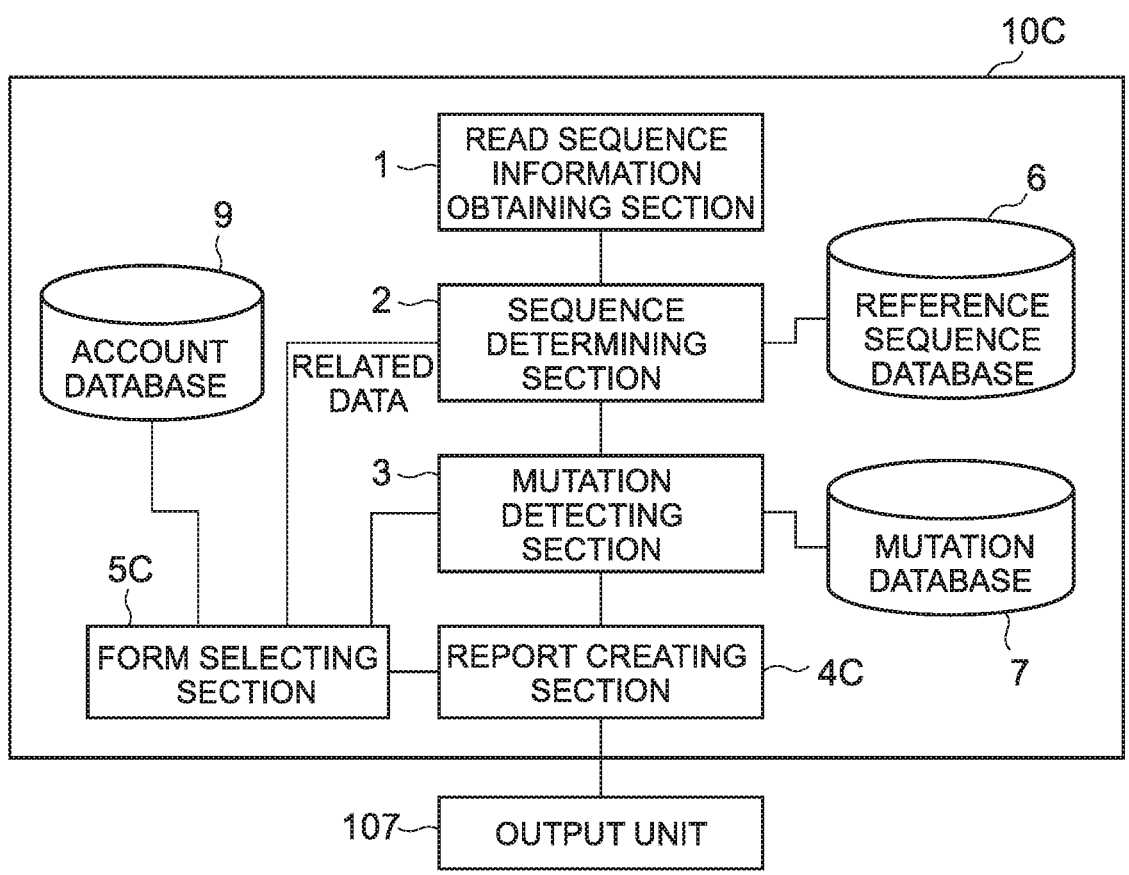
FIG. 27 is a functional block diagram illustrating a nucleic acid sequence analysis and presentation apparatus 10C.

FIG. 27 illustrates an exemplary functional block diagram for functions related to nucleic acid sequence analysis and presentation processing by the nucleic acid sequence analysis and presentation apparatus 10C. The nucleic acid sequence analysis and presentation apparatus 10C includes a read sequence information obtaining section 1, a sequence determining section 2, a mutation detecting section 3, a report creating section 4C, a form selecting section 5C, a reference sequence database 6, a mutation database 7, and an account database 9.

The account database 9 may be stored in the storage device 103 of the control unit 100 illustrated in FIG. 8. The account database 9 stores, for example, data illustrated in FIG. 28. In FIG. 28, ID is an identifier for identifying a reader of a report. A disclosure policy may specify a policy about disclosure of information on a germline mutation. An informed consent specifies whether a patient consents to disclose information on a germline mutation to himself/herself. For example, ID: AAA indicates disclosing all the information on a germline mutation irrespective of whether the patient gives an informed consent (N/A). Such account may be acquired by, for example, a gene analysis expert, an attending doctor who desires to know information on a germline mutation of the patient, and the like. Then, ID: BBB indicates disclosing all the information on a germline mutation because the patient consents to disclose the information on the germline mutation to himself/herself in the informed consent. Such account may be acquired by, for example, a gene analysis expert, an attending doctor who desires to know information on a germline mutation of the patient, and the patient himself/herself who desires to know the information on the germline mutation. ID: CCC indicates treating all the information on a germline mutation (an incidental finding) as confidential because the patient does not consent to disclose the information on the germline mutation to himself/herself in the informed consent. Such account may be acquired by a patient who does not consent to disclose information on a germline mutation to himself/herself in the informed consent, an attending doctor who does not desire to know the information on the germline mutation of the patient, and the like.

Nucleic Acid Sequence Analysis and Presentation Processing 1 by Nucleic Acid Sequence Analysis and Presentation Apparatus 10C The presentation apparatus 10C is accessible through a network such, for example, as a cloud from an external computer by any of the above account holders.

FIG. 29 illustrates nucleic acid sequence analysis and presentation processing by the nucleic acid sequence analysis and presentation apparatus 10C. The read sequence information obtaining section 1 obtains read sequence data at step ST41 in FIG. 29A.

At step ST42a in FIG. 29A, the sequence determining section 2 executes the processes at steps ST2 to ST5 in FIG. 11 to align each of a normal read sequence and a tumor read sequence with the reference sequence.

At step ST42b in FIG. 29A, the mutation detecting section 3 executes the processes at steps ST23 to ST27 in FIG. 14 and steps ST13 to ST16 in FIG. 16 to detect a somatic mutation and a germline mutation and give the annotations.

The report creating section 4C and the form selecting section 5C do not select or create an analysis report but wait until the user having the account makes an access.

When the user having the account starts to access the control unit 100 through the I/F unit 105 of the presentation apparatus 10C via the network, the report creating section 4C and the form selecting section 5C start the processing of selecting and creating the analysis report.

At step ST141 in FIG. 29B, the form selecting section 5C acquires log-in information transmitted by the user having the account through the I/F unit 105 and accepts the log-in.

At step ST142, the form selecting section 5C receives a report output request transmitted by the user having the account.

When the form selecting section 5C determines that a germline mutation is present at step ST143 (in the case of "Yes"), the processing proceeds to step ST144.

At step ST144, the form selecting section 5C checks if the account ID contained in the account information transmitted by the user matches any one of the account IDs stored in the account database 9. And, for example, when the account ID is "CCC" as shown in FIG. 28, the form selecting section 5c determines that it is necessary to treat the incidental finding as confidential according to the disclosure policy about disclosure of information on a germline mutation (Yes). Then, the processing proceeds to step ST145.

At step ST145, the report creating section 4C creates an analysis report in the confidential form in the same manner as at step ST105 in FIG. 20.

When the form selecting section 5C determines that no germline mutation is present (in the case of "No", at step ST143) or when the form selecting section 5C determines that it is unnecessary to treat the incidental finding as confidential ("No", at step ST144) because the account ID is "AAA" or "BBB", the processing proceeds to step ST146 and the report creating section 4C creates the normal report R1 illustrated in FIG. 2 in the normal form.

Nucleic Acid Sequence Analysis and Presentation Processing 2 by Nucleic Acid Sequence Analysis and Presentation Apparatus 10C The presentation apparatus 10C is accessible through a network such, for example, as a cloud from an external computer by any of the above account holders.

Figure 30A:
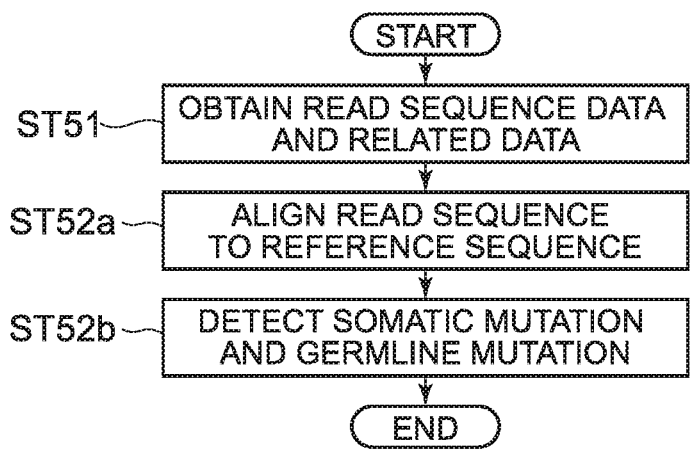
FIGS. 30A and 30B are flow diagrams illustrating other processing executed by a nucleic acid sequence analysis and presentation apparatus 10C.

Using FIG. 30, description is given of a modified example of the nucleic acid sequence analysis and presentation processing by the nucleic acid sequence analysis and presentation apparatus 10C. Steps ST51 and ST52 in FIG. 30A are the same as steps ST41 and ST42 in FIG. 29A.

Figure 30B:
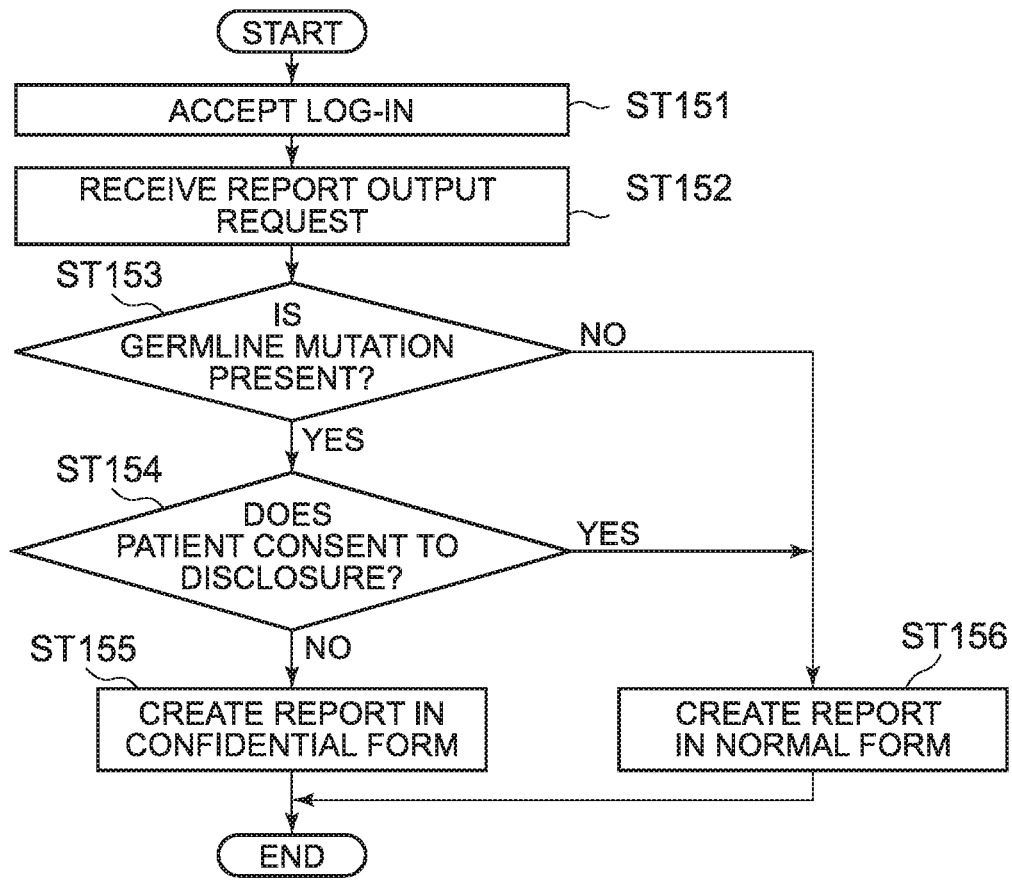

Steps ST151, ST152, ST153, ST155, and ST156 in FIG. 30B are the same as steps ST141, ST142, ST143, ST145, and ST146 in FIG. 29B.

Figure 31:
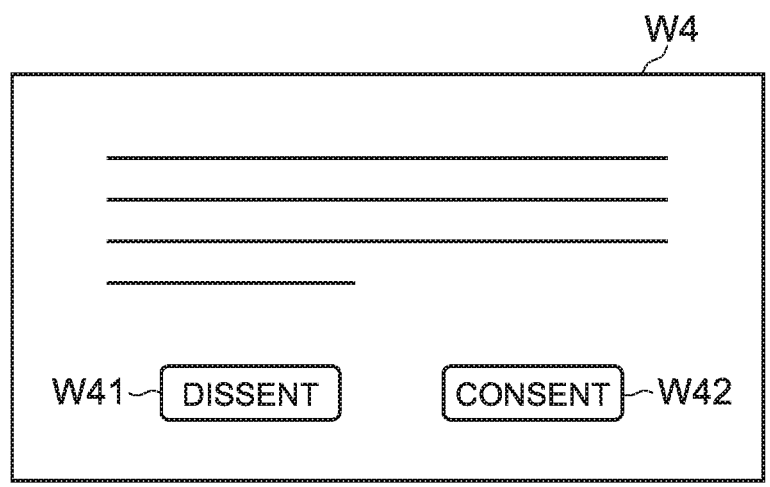
FIG. 31 is a diagram illustrating an example of a dialog for prompting a user to select whether to consent to be informed of information on a germline mutation.

At step ST154, the form selecting section 5C checks if the account ID contained in the account information transmitted by the user marches any one of the account IDs stored in the account database 9, and causes a dialog W4 illustrated in FIG. 31 to be displayed on a display of the computer of the user. The dialog W4 contains a "DISSENT" icon W41 and a "CONSENT" icon W42 for confirming whether the patient or the user consents to disclose information on a germline mutation. When the control unit 100 receives a selection of the "DISSENT" icon W41 made by the patient or the user, the processing proceeds to step ST155. When the control unit 100 receives a selection of the "CONSENT" icon W42 made by the patient or the user, the processing proceeds to step ST156.

(Nucleic Acid Sequence Analysis and Presentation Apparatus 10D)

Configuration of Nucleic Acid Sequence Analysis and Presentation Apparatus 10D

A hardware configuration of a nucleic acid sequence analysis and presentation apparatus 10D is the same as that of the nucleic acid sequence analysis and presentation apparatus 10 illustrated in FIG. 8. Even when the user selects creation of an analysis report in the form of the confidential report R2, the nucleic acid sequence analysis and presentation apparatus 10D may create an analysis report in the presentation form of the confidential report R3 or the confidential report R4 if a germline mutation is detected in a particular gene.

Figure 32:
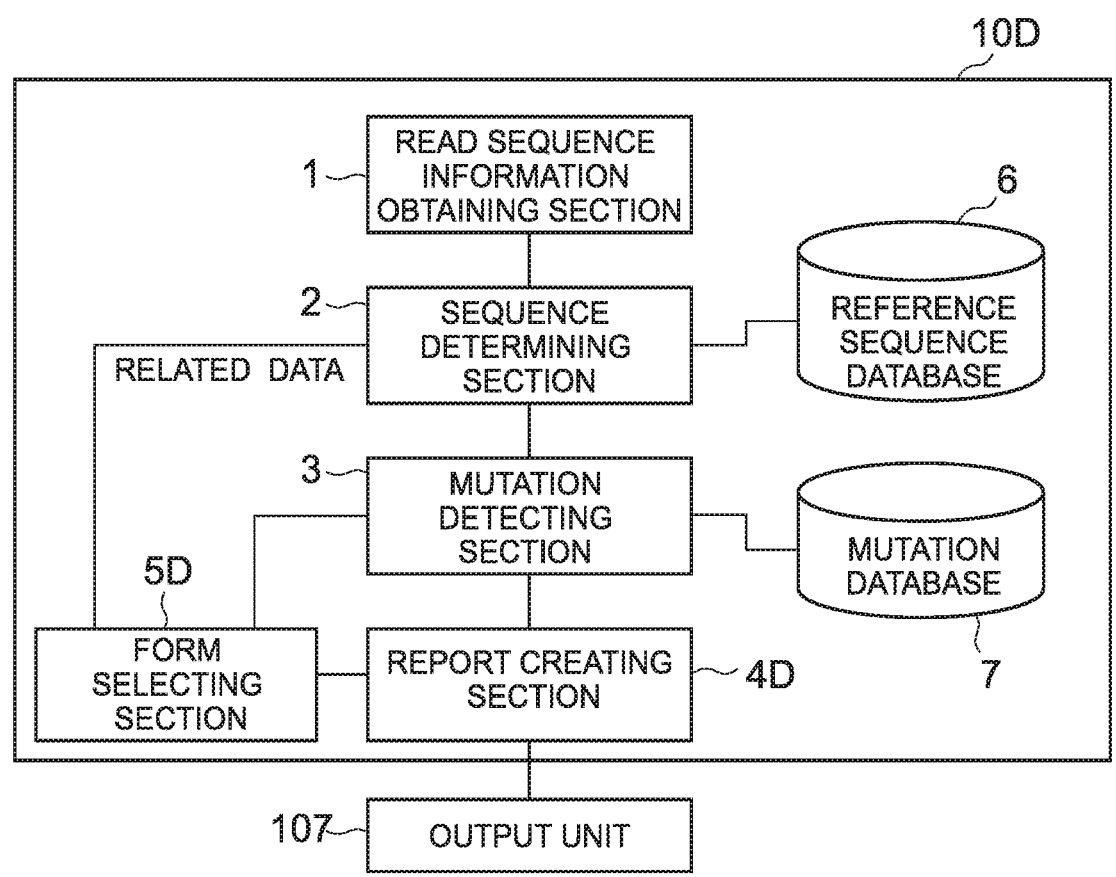
FIG. 32 is a functional block diagram illustrating a nucleic acid sequence analysis and presentation apparatus 10D.

FIG. 32 illustrates an exemplary functional block diagram for functions related to nucleic acid sequence analysis and presentation processing by the nucleic acid sequence analysis and presentation apparatus 10D. The nucleic acid sequence analysis and presentation apparatus 10D includes a read sequence information obtaining section 1, a sequence determining section 2, a mutation detecting section 3, a report creating section 4D, a form selecting section 5D, a reference sequence database 6, and a mutation database 7.

Figure 33:
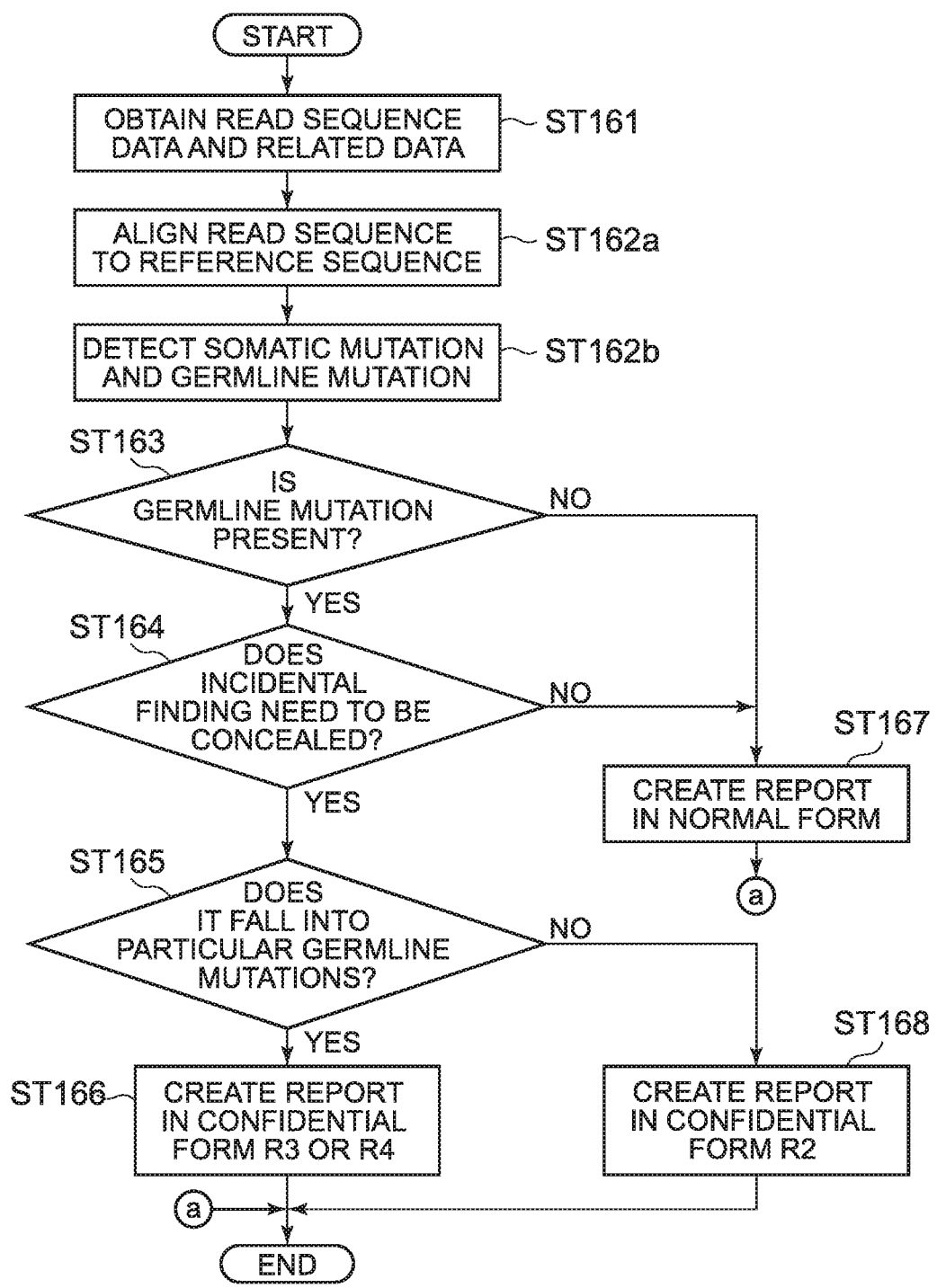
FIG. 33 is a flow diagram illustrating other processing executed by a nucleic acid sequence analysis and presentation apparatus 10D.

Nucleic Acid Sequence Analysis and Presentation Processing by Nucleic Acid Sequence Analysis and Presentation Apparatus 10D Using FIG. 33, it is described the nucleic acid sequence analysis and presentation processing by the nucleic acid sequence analysis and presentation apparatus 10D. Steps ST161 to ST164 and ST167 in FIG. 33 are the same as steps ST111 to ST114 and ST116 in FIG. 23, respectively.

At step ST165, the form selecting section 5D determines whether the germline mutation detected at step ST163 falls under the particular germline mutations listed in FIG. 6, for example. When the germline mutation falls under the particular germline mutations (in the case of "Yes"), the form selecting section 5D advances the processing to step ST166 even though the confidential form selected in advance is the form of the confidential report R2 to treat entire information on a germline mutation as confidential, and the report creating section 4D creates an analysis report in the form of the confidential report R3 or R4 to disclose at least part of information on a germline mutation.

When the form selecting section 5D determines that the germline mutation detected at step ST163 does not fall under the particular germline mutations (No) at step ST165, the processing proceeds to step ST168 and the report creating section 4D creates an analysis report in the form of the confidential report R2 or the selected form other than the confidential report R2.

(Nucleic Acid Sequence Analysis and Presentation Apparatus 10E)

Configuration of Nucleic Acid Sequence Analysis and Presentation Apparatus 10E

A hardware configuration of a nucleic acid sequence analysis and presentation apparatus 10E is the same as that of the nucleic acid sequence analysis and presentation apparatus 10 illustrated in FIG. 8. The nucleic acid sequence analysis and presentation apparatus 10E changes the presentation form of an analysis report according to the disease name of the patient in the prescribed information obtained as the related data by the presentation apparatus 10E.

Figure 34:
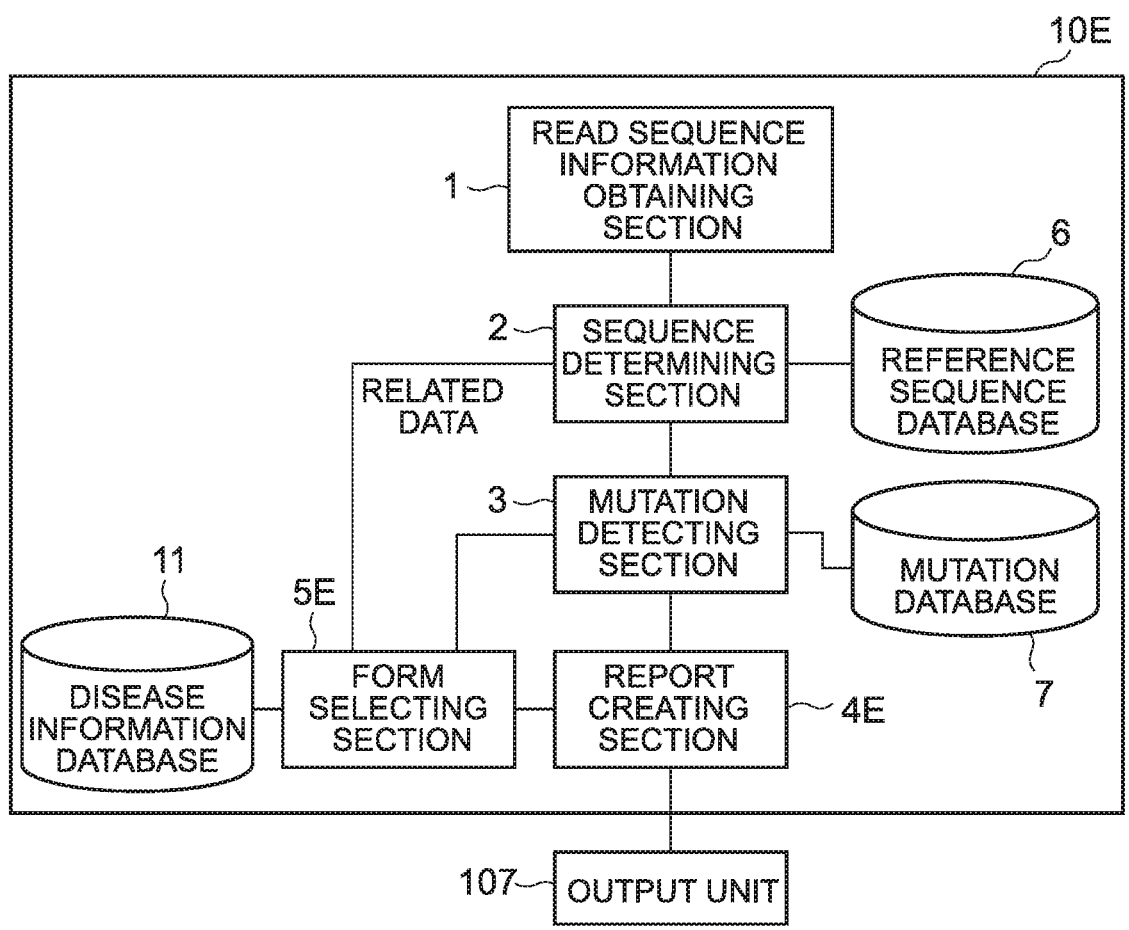
FIG. 34 is a functional block diagram illustrating a nucleic acid sequence analysis and presentation apparatus 10E.

FIG. 34 illustrates an exemplary functional block diagram for functions related to nucleic acid sequence analysis and presentation processing by the presentation apparatus 10E. The nucleic acid sequence analysis and presentation apparatus 10E includes a read sequence information obtaining section 1, a sequence determining section 2, a mutation detecting section 3, a report creating section 4E, a form selecting section 5E, a reference sequence database 6, a mutation database 7, and a disease information database 11.

The disease information database 11 illustrated in FIG. 35 may be stored in the storage device 103. In the example illustrated in FIG. 35, a gene name and a mutation position for which a germline mutation was reported are stored in association with a related disease(s) in the disease information database 11.

Figure 36:
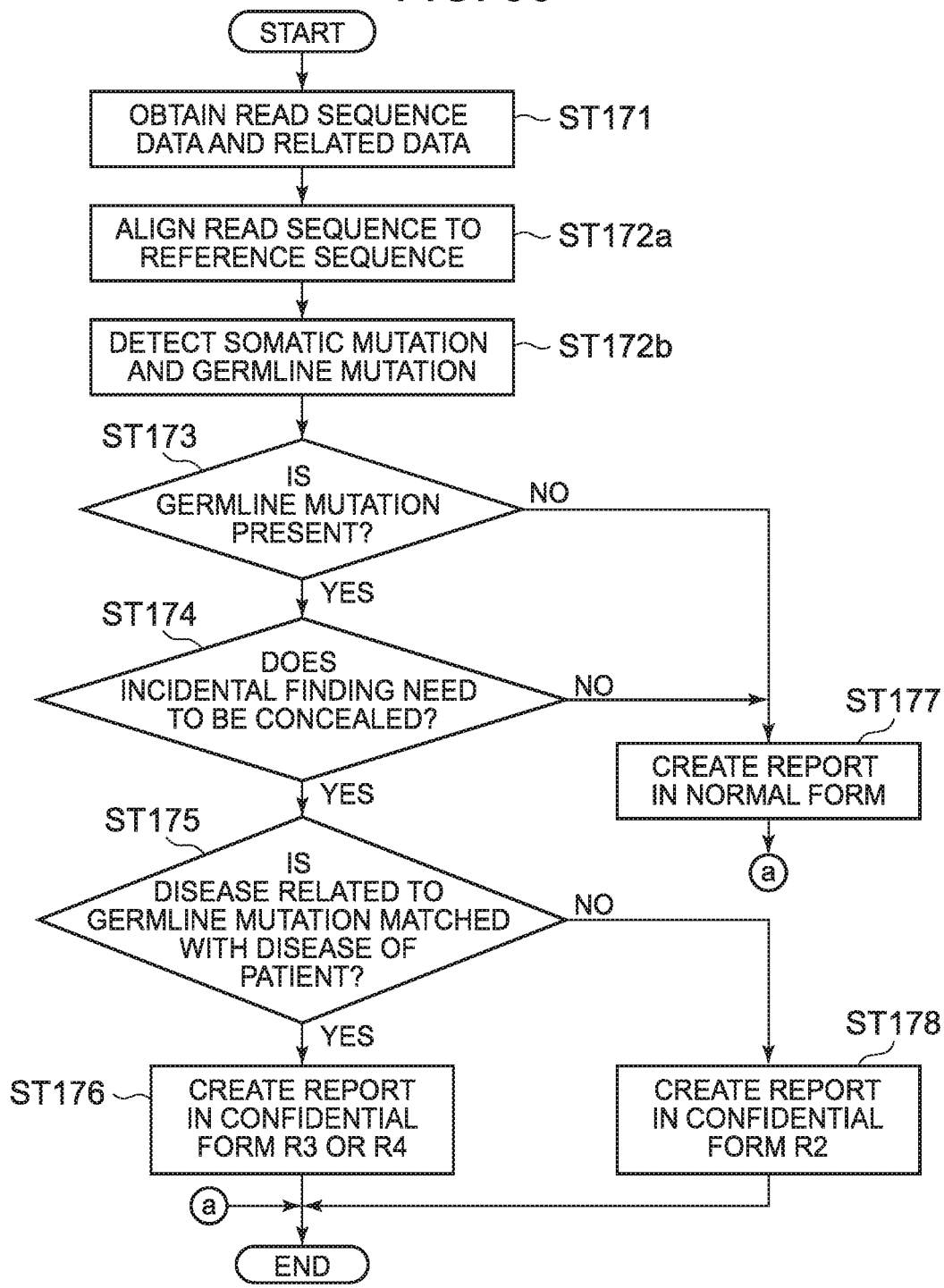
FIG. 36 is a flow diagram illustrating other processing executed by a nucleic acid sequence analysis and presentation apparatus 10E.

Nucleic Acid Sequence Analysis and Presentation Processing by Nucleic Acid Sequence Analysis and Presentation Apparatus 10E Using FIG. 36, it is described the nucleic acid sequence analysis and presentation processing by the nucleic acid sequence analysis and presentation apparatus 10E. Steps ST171 to ST174, ST176, ST177, and ST178 in FIG. 36 are the same as steps ST161 to ST164, ST166, ST167, and ST168 in FIG. 33.

At step ST175, the form selecting section 5E checks if the gene name for which the germline mutation is detected at step ST173 matches the disease information database 11. When the gene name for which the germline mutation is detected at step ST173 is present in the disease information database 11, the form selecting section 5E checks if the disease name related to the concerned gene matches the disease name of the patient inputted at step ST171. When the disease related to the germline mutation detected at step ST173 is matched with the disease name of the patient inputted at step ST171 (in the case of "Yes"), the form selecting section 5E advances the processing to step ST176 and the report creating section 4E creates an analysis report in the form of the confidential report R3 or R4 to disclose at least part of information on a germline mutation even if the confidential form selected in advance is the form of the confidential report R2 to treat entire information on a germline mutation as confidential.

Meanwhile, when the disease related to the germline mutation detected at step ST173 is not matched with the disease name of the patient inputted at step ST171 (in the case of "No") at step ST175, the form selecting section 5E advances the processing to step ST177 and the report creating section 4E creates an analysis report in the form of the confidential report R2 or the selected form other than the confidential report R2.

[Computer Program]

Steps ST1 to ST5 in FIG. 11, steps ST21 to ST27 in FIG. 14, and steps ST11 to ST16 in FIG. 16 may be executed on a computer as a computer program for nucleic acid sequence analysis. Steps ST101 to ST106 in FIG. 20, steps ST111 to ST116 in FIG. 23, steps ST131 to ST137 in FIG. 26, steps ST141 to ST146 in FIG. 29, steps ST151 to ST156 in FIG. 30, steps ST161 to ST168 in FIG. 33, and steps ST171 to ST178 in FIG. 36 may be executed on a computer as a computer program for presentation of a nucleic acid sequence analysis result.

In addition, the aforementioned computer programs may be provided as program products stored in storage media or the like. The aforementioned computer programs may be stored in storage media such as hard disks, semiconductor memory elements such as flash memories, and optical disks. The storage format of the programs in the storage media is not limited as long as the control unit can read the programs stored in that format. The programs are preferably stored in the storage media in a non-volatile manner.

OTHER EMBODIMENTS

Embodiments should not be interpreted by being limited to the above-described embodiments.

Figure 37:
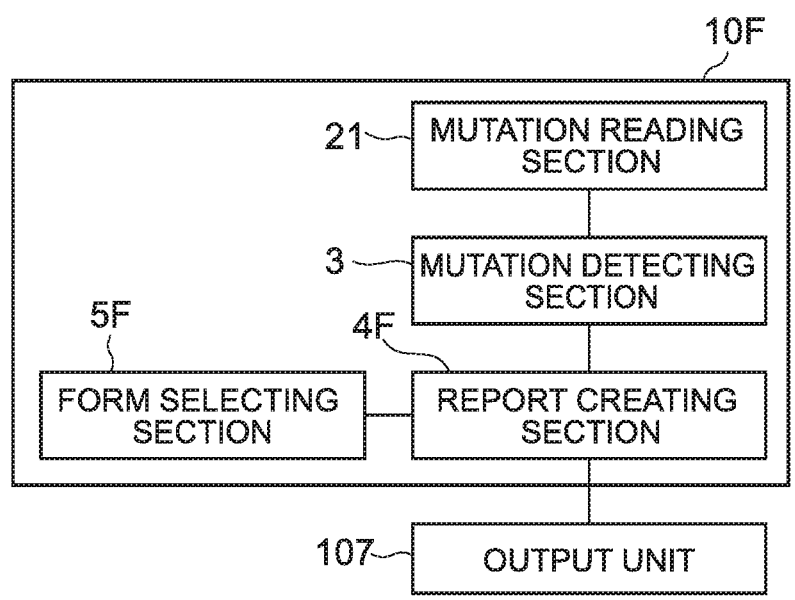
FIG. 37 is a functional block diagram illustrating a presentation apparatus 10F.

The above-described nucleic acid sequence analysis and presentation apparatuses 10A to 10E are each described as an apparatus that analyzes mutations. Instead, an apparatus only having the function to select the presentation form of an analysis report and the function to create the analysis reports R1, R2, R3, and R4 and an apparatus that analyzes mutations may be separate from each other. In addition, the apparatus that analyzes mutations may be incorporated in the sequencer 30. FIG. 37 illustrates a functional block diagram of a presentation apparatus 10F only having the function to create the analysis reports R1, R2, R3, and R4. A hardware configuration of the presentation apparatus 10F is the same as that of the nucleic acid sequence analysis and presentation apparatus 10 illustrated in FIG. 8. The presentation apparatus 10F includes a mutation reading section 21, a report creating section 4F, and a form selecting section 5F. The mutation reading section 21 receives, for example, the information on mutations detected at step ST103b in FIG. 20 through the input unit 106. The report creating section 4F and the form selecting section 5F may have the same functions as any of the report creating sections 4A to 4E and any of the form selecting sections 5A to 5E, respectively.

The invention claimed is:

1. An analysis method of analyzing a nucleic acid sequence derived from a patient sample with a computer, the computer configured with instructions to perform operations comprising:
   obtaining from a storage device or a sequencer coupled to the computer, nucleic acid sequence data related to the nucleic acid sequence derived from the patient sample and reference sequence data;
   determining a presence of a mutation by:
      comparing the obtained nucleic acid sequence data with the reference sequence data;
      identifying whether a rate of coincidence between the nucleic acid sequence data and the reference sequence data satisfies a predetermined criteria; and
      generating an analysis result based on the comparison;
   receiving a selection from among candidate forms each for the same patient associated with the patient sample, the candidate forms comprising a first form and a second form different from the first form, for providing a report of information of the patient and the analysis result based on the determination of the presence of the mutation; and
   generating, based on the received selection being the first form, a first report of the analysis result providing information relating to the determined mutation in the first form which is different from the second form, and generating based on the received selection being the second form, a second report of the analysis result providing information relating to the determined mutation in the second form which is different from the first form, wherein
   the second report includes the information of the patient and provides information relating to a germline mutation among the determined mutation in the second form, and
   the first report includes the information of the patient and does not provide at least part of the information relating to the germline mutation.

2. The analysis method according to claim 1, wherein the first report provides information relating to the determined mutation in the first form without explicit indication that the determined mutation includes the germline mutation.

3. The analysis method according to claim 1, wherein the first report provides a mutation position of the determined mutation.

4. The analysis method according to claim 1, wherein the first report provides a mutation position of the determined mutation without explicit indication that the determined mutation includes the germline mutation.

5. The analysis method according to claim 1, further comprising receiving account information of a reader of the analysis result of the nucleic acid sequence derived from the patient, wherein
the first report does not provide at least part of the information relating to the germline mutation when the account information indicates that an incidental finding regarding the determined mutation is to be treated as confidential, the incidental finding comprising a nucleic acid sequence mutation other than the determined mutation, which presents in a tumor cell.

6. The analysis method according to claim 1, wherein the first report further provides information on the patient.

7. The analysis method according to claim 6, wherein the second report further provides information on the mutation and a gene in which the mutation is detected.

8. The analysis method according to claim 1, further comprising
generating the second report.

9. The analysis method according to claim 1, wherein
the receiving the selection comprises receiving prescribed information that indicates a presentation form of the information relating to the germline mutation.

10. A system that analyzes a nucleic acid sequence derived from a patient sample, comprising:
a memory storing instructions; and
a processor in communication with the memory, the processor configured with the instructions to cause the system to perform operations comprising:
obtaining from a storage device or a sequencer coupled to the system, nucleic acid sequence data related to the nucleic acid sequence derived from the patient sample and reference sequence data;
determining a presence of a mutation by comparing the obtained nucleic acid sequence data with the reference sequence data and identifying whether a rate of coincidence between the nucleic acid sequence data and the reference sequence data satisfies a predetermined criteria, and generating an analysis result;
receiving a selection from among candidate forms for the same patient associated with the patient sample, the candidate forms comprising a first form and a second form different from the first form, for providing a report of information of the patient and the analysis result based on the determination of the presence of the mutation; and
generating, based on the received selection being the first form, a first report of the analysis result providing information relating to the determined mutation in the first form which is different from the second form, and generating based on the received selection being the second form, a second report of the analysis result providing information relating to the determined mutation in the second form which is different from the first form, wherein
the second report includes the information of the patient and provides information relating to a germline mutation among the determined mutation in the second form and
the first report includes the information of the patient and does not provide at least part of the information relating to the germline mutation.

11. The system according to claim 10, wherein the first report provides information relating to the determined mutation in the first form without explicit indication that the determined mutation includes the germline mutation.

12. The system according to claim 10, wherein the first report provides a mutation position of the determined mutation.

13. The system according to claim 10, wherein the first report provides a mutation position of the determined mutation without explicit indication that the determined mutation includes the germline mutation.

14. The system according to claim 10, wherein the processor is configured with the instructions to cause the system to perform operations further comprising receiving account information of a reader of the analysis result of the nucleic acid sequence derived from the patient,
wherein the first report does not provide at least part of the information relating to the germline mutation when the account information indicates that an incidental finding regarding the determined mutation is to be treated as confidential, the incidental finding comprising a nucleic acid sequence mutation other than the determined mutation, which presents in a tumor cell.

15. The system according to claim 10, wherein the first report further provides information on the patient, and
the second report further provides information on the mutation and a gene in which the mutation is detected.

16. The system according to claim 10, wherein the processor is configured to cause the system to perform operations further comprising generating the second report.

17. The system according to claim 10, wherein the receiving the selection comprises receiving prescribed information that indicates a presentation form of the information relating to the germline mutation.

* * * * *

SEQUENCE LISTING

<160> NUMBER OF SEQ ID NOS: 5

<210> SEQ ID NO 1
<211> LENGTH: 23

```
<212> TYPE: DNA
<213> ORGANISM: Homo sapiens

<400> SEQUENCE: 1
gccatggaca gaaggcgcag ggc                                           23

<210> SEQ ID NO 2
<211> LENGTH: 13
<212> TYPE: DNA
<213> ORGANISM: Homo sapiens

<400> SEQUENCE: 2
ggcatggaca gaa                                                      13

<210> SEQ ID NO 3
<211> LENGTH: 13
<212> TYPE: DNA
<213> ORGANISM: Homo sapiens

<400> SEQUENCE: 3
gccatgcaca gaa                                                      13

<210> SEQ ID NO 4
<211> LENGTH: 15
<212> TYPE: DNA
<213> ORGANISM: Homo sapiens

<400> SEQUENCE: 4
gccatggaca gggcg                                                    15

<210> SEQ ID NO 5
<211> LENGTH: 20
<212> TYPE: DNA
<213> ORGANISM: Homo sapiens

<400> SEQUENCE: 5
gccatggacg tcagaaggcg                                               20
```